US010716485B2

(12) United States Patent
Krishnaswamy et al.

(10) Patent No.: US 10,716,485 B2
(45) Date of Patent: Jul. 21, 2020

(54) DEEP BRAIN SOURCE IMAGING WITH M/EEG AND ANATOMICAL MRI

(71) Applicants: THE GENERAL HOSPITAL CORPORATION, Boston, MA (US); MASSACHUSETTS INSTITUTE OF TECHNOLOGY, Boston, MA (US)

(72) Inventors: Pavitra Krishnaswamy, Boston, MA (US); Patrick Purdon, Somerville, MA (US); Gabriel Obregon-Henao, Boston, MA (US); Matti Hamalainen, Boston, MA (US); Behtash Babadi, Allston, MA (US)

(73) Assignees: The General Hospital Corporation, Boston, MA (US); Massachusetts Institute of Technology, Boston, MA (US)

( * ) Notice: Subject to any disclaimer, the term of this patent is extended or adjusted under 35 U.S.C. 154(b) by 372 days.

(21) Appl. No.: 15/521,987

(22) PCT Filed: Nov. 9, 2015

(86) PCT No.: PCT/US2015/059751
§ 371 (c)(1),
(2) Date: Apr. 26, 2017

(87) PCT Pub. No.: WO2016/073985
PCT Pub. Date: May 12, 2016

(65) Prior Publication Data
US 2017/0332933 A1 Nov. 23, 2017

Related U.S. Application Data

(60) Provisional application No. 62/076,525, filed on Nov. 7, 2014.

(51) Int. Cl.
*A61B 5/0436* (2006.01)
*A61B 5/0476* (2006.01)
(Continued)

(52) U.S. Cl.
CPC .......... *A61B 5/0436* (2013.01); *A61B 5/0476* (2013.01); *A61B 5/055* (2013.01); *A61B 5/4064* (2013.01)

(58) Field of Classification Search
CPC ... A61B 5/0436; A61B 5/4064; A61B 5/0476; A61B 5/055; A61B 5/7285;
(Continued)

(56) References Cited

U.S. PATENT DOCUMENTS

2007/0223731 A1* 9/2007 Togami .................. H04R 3/005
381/92
2011/0222781 A1* 9/2011 Nguyen ............... G06K 9/6244
382/218

(Continued)

OTHER PUBLICATIONS

Attal et al. "Assessment of Subcortical Source Localization Using Deep Brain Activity Imaging Model with Minimum Norm Operators : A MEG Study"; PLoS One, vol. 8, No. 3; Mar. 20 (Year: 2013).*

(Continued)

*Primary Examiner* — Theodore J Stigell
*Assistant Examiner* — Amy J Shafqat
(74) *Attorney, Agent, or Firm* — Quarles & Brady LLP

(57) ABSTRACT

A method for non-invasively resolving electrophysiological activity in sub-cortical structures located deep in the brain by comparing amplitude-insensitive M/EEG field patterns arising from activity in subcortical and cortical sources under physiologically relevant sparse constraints is disclosed. The method includes a sparse inverse solution for M/EEG subcortical source modeling. Specifically, the method employs a subspace-pursuit algorithm rooted in (Continued)

compressive sampling theory, performs a hierarchical search for sparse subcortical and cortical sources underlying the measurement, and estimates millisecond-scale currents in these sources to explain the data. The method can be used to recover thalamic and brainstem contributions to non-invasive M/EEG data, and to enable non-invasive study of fast timescale dynamical and network phenomena involving widespread regions across the human brain.

20 Claims, 14 Drawing Sheets

(51) Int. Cl.
*A61B 5/055* (2006.01)
*A61B 5/00* (2006.01)

(58) Field of Classification Search
CPC .... A61B 2090/3954; A61B 2562/0223; A61B 5/04004; A61B 5/04012; A61B 2018/00839; A61B 5/0006; A61B 5/0042; A61B 5/04008; G01R 33/5673; G01R 33/567; G01R 33/58; G01R 33/20; G01R 33/34084; G01R 33/4806; G01R 33/4836; G06T 7/00; G06T 2207/10088; G06T 2207/10141; G06T 2207/10148; G06T 2207/20012; G06T 2207/30016; G01N 24/00; G06F 3/015; G06F 2203/011; G10H 2220/376; G10H 2220/381; G10H 2220/371; G10H 2250/161; H04N 21/42201; A61N 1/0531

See application file for complete search history.

(56) References Cited

U.S. PATENT DOCUMENTS

| | | | |
|---|---|---|---|
| 2014/0003695 A1* | 1/2014 | Dean | G06T 7/0012 382/131 |
| 2014/0066739 A1 | 3/2014 | He et al. | |
| 2014/0155730 A1* | 6/2014 | Bansal | G01V 3/14 600/409 |
| 2014/0323897 A1* | 10/2014 | Brown | A61B 5/4821 600/544 |
| 2016/0045128 A1* | 2/2016 | Sitt | A61B 5/7246 600/409 |
| 2016/0081577 A1* | 3/2016 | Sridhar | A61B 5/4064 600/383 |
| 2016/0157742 A1* | 6/2016 | Huang | A61B 5/7203 600/409 |

OTHER PUBLICATIONS

W. Dai and O. Milenkovic, "Subspace pursuit for compressive sensing: Closing the gap between performance and complexity," CoRR, vol.abs/0803.0811 (Year: 2008).*

International Search Report and Written Opinion for International Application No. PCT/US2015/059751 dated Jan. 29, 2016.

Babadi et al., A Subspace Pursuit-based Interative Greedy Hierarchical Solution to the Neuromagnetic Inverse Problem, Neuroimage, vol. 87, Feb. 2014.

Attal et al., Assessment of Subcortical Source Localization Using Deep Brain Activity Imaging Model with Minimum Norm Operators: A MEG Study, PLoS Ine, vol. 8, No. 3, Mar. 20, 2013.

* cited by examiner (A) Cortical Surface Decomposed to Patches of Varying Sizes

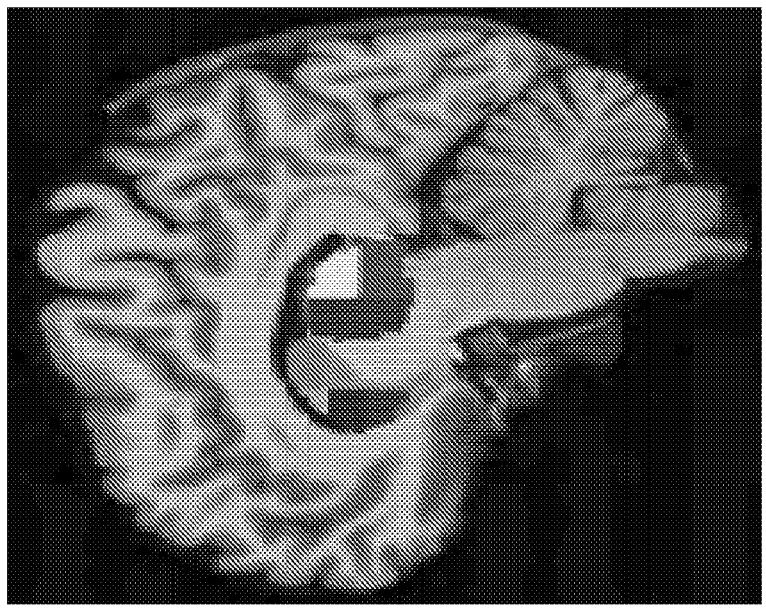
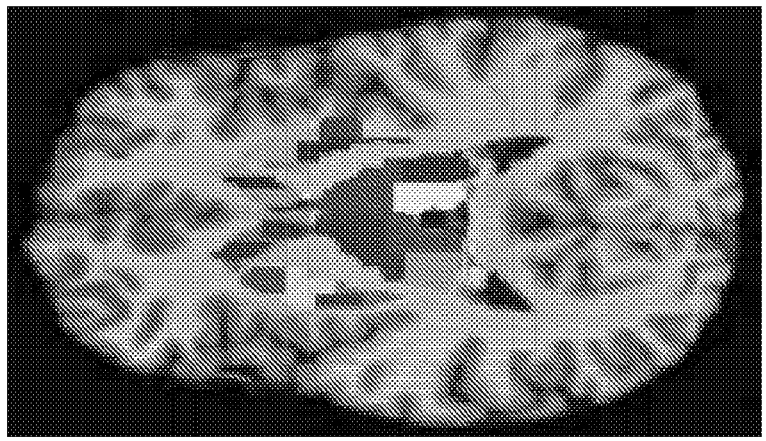
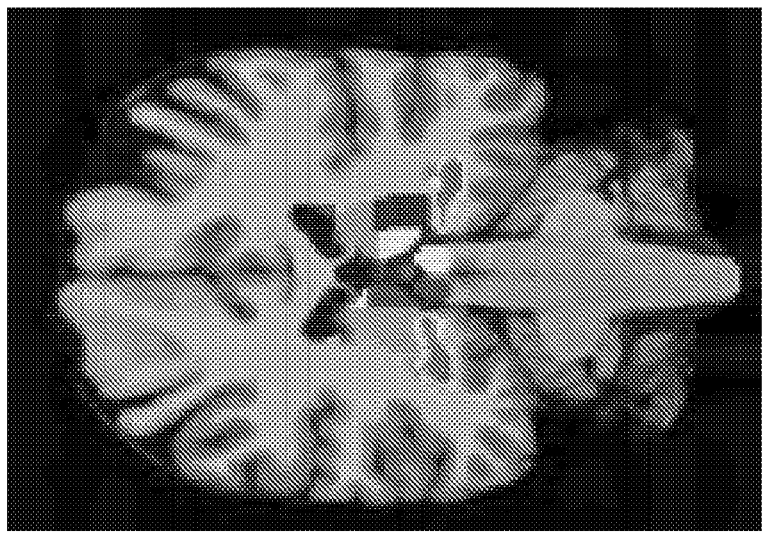
(B) Subcortical Volumes Comprising Subdivided Anatomic Segmentations
FIG. 3C

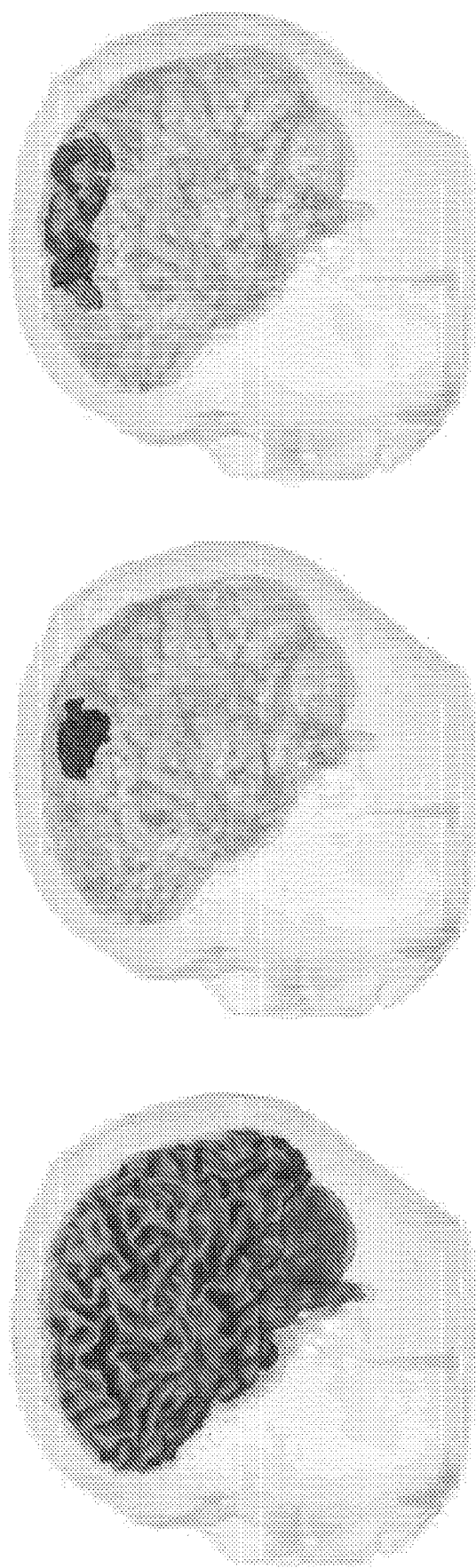
(A) Start with Full Brain  FIG. 5A
(B) Find Sparse Cortical Solution  FIG. 5B
(C) Finer Search in Neighborhood of Sparse Cortical Solution  FIG. 5C

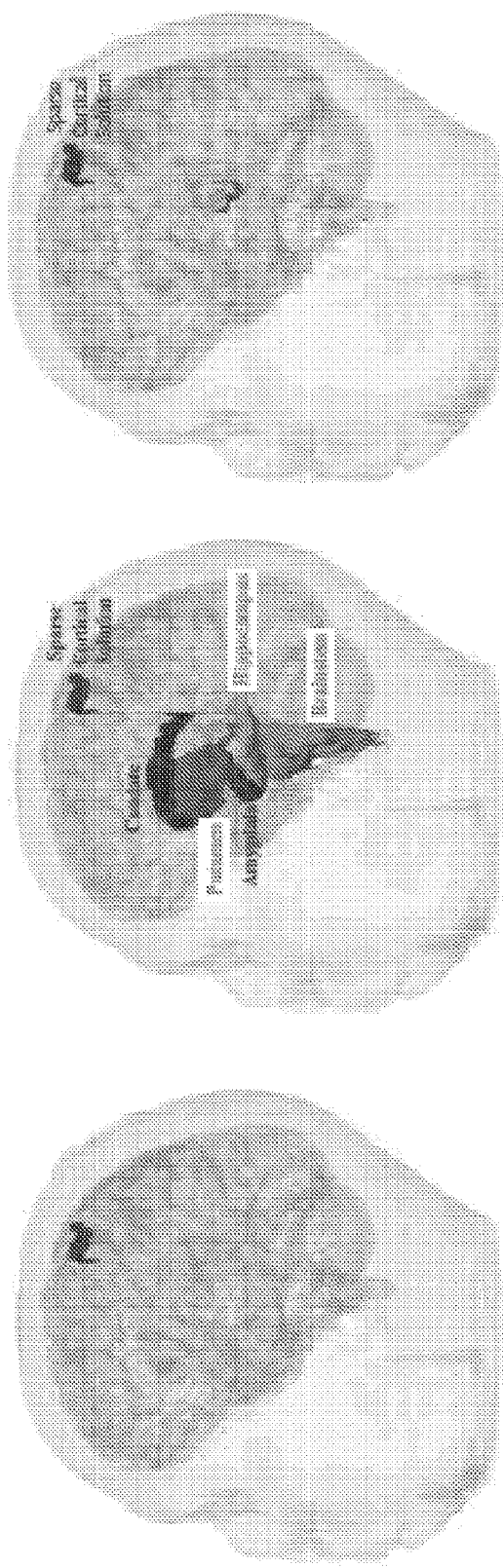

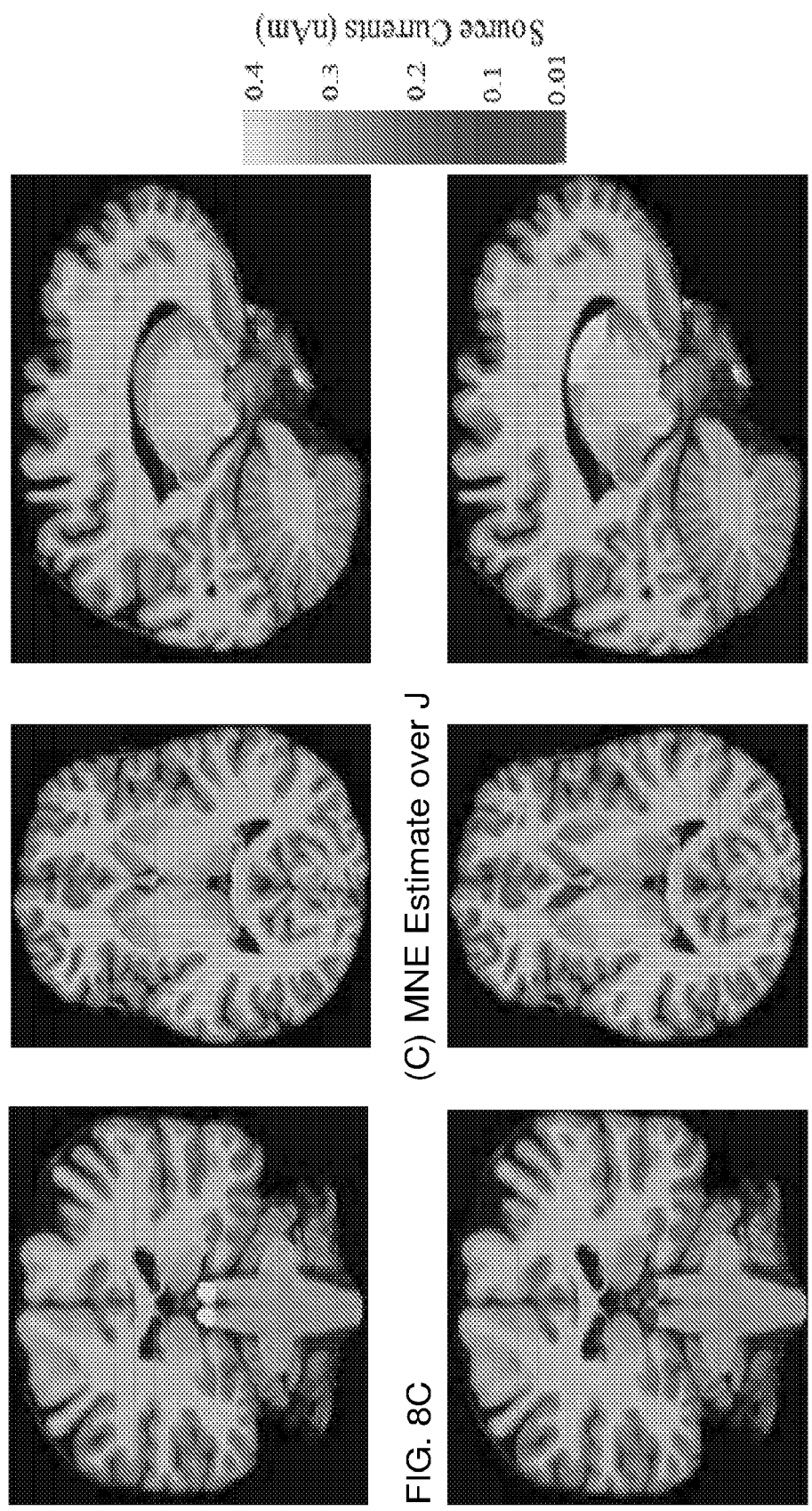

(D) Regional Current Distribution (E) Subspace Pursuit Estimates (F) MNE Estimates

DEEP BRAIN SOURCE IMAGING WITH M/EEG AND ANATOMICAL MRI

CROSS-REFERENCE TO RELATED APPLICATIONS

This application represents the U.S. National Stage of International Application No. PCT/US2015/059751, filed Nov. 9, 2015 which claims the benefit of U.S. Provisional patent application Ser. No. 62/076,525 filed on Nov. 7, 2014, which is incorporated herein by reference.

BACKGROUND

Understanding human brain function in cognition, behavior and illness remains an enduring challenge. This is because the brain is highly complex, with billions of neurons, interacting dynamically to receive, process, retrieve, transmit, and store information. Neurons signal via millisecond electrical impulses, communicate with other neurons in both local (mm-range) and distant (cm-range) regions. These interactions evolve instantaneously in response to external stimuli, drugs, or feedback from other brain regions, during creation and expression of memory, emotion and perception, across states of arousal, and over time due to plasticity, learning, development and aging. Thus, many scientific challenges in understanding brain function come about from the need to parse these complex dynamical interactions across diverse spatial and temporal scales, such as across superficial cortical and deeper subcortical regions, and on time scales ranging from milliseconds to seconds and minutes. Monitoring these complex dynamic interactions at the relevant spatial and temporal scales, and as they occur in normal, clinical and disease states is, however, technologically challenging using known methods.

Electrophysiological techniques to assess neuronal activity serve as direct indicators of neuronal currents, neuronal spiking or postsynaptic potentials, and have uniquely high temporal resolution on the order of milliseconds. These techniques can be either invasive or non-invasive.

Invasive electrophysiological measurement techniques (e.g., electrocorticography) can be employed in patient populations with surgically implanted intracranial electrodes. While these techniques provide high spatial and temporal resolution of regional neuronal dynamics, they are highly invasive, and thus are typically applied in critical clinical settings (such as during surgery). This limits the types of patients/subjects, cognitive tasks, and behaviors that can be monitored with such techniques. Further, invasive electrophysiological techniques are limited to the focal regions wherein recording electrodes are placed (typically superficial cortical areas). Therefore, these techniques have limited spatial span for characterizing deep subcortical regions that have critical roles in a variety of cognitive and clinically relevant brain states.

Non-invasive electrophysiological measurement techniques such as electroencephalography (EEG) and magnetoencephalography (MEG) are widely used in human neuroscience studies. M/EEG techniques are non-invasive, and can therefore be used to monitor and measure brain activities across a variety of patients/subjects, as well as in many types of cognitive tasks and behaviors. M/EEG techniques comprise data from sensors distributed across the head, and measure, with millisecond-resolution, electromagnetic fields generated by neuronal currents all over the brain. However, the data do not directly pinpoint spatial locations or regions where the neuronal currents originate. Instead, the locations have to be spatially resolved by computing appropriate solutions to the electromagnetic inverse problem of recovering regional current distributions from M/EEG data. This method is termed as electromagnetic source imaging, and offers a unique means to non-invasively probe regional brain dynamics with high temporal resolution.

FIG. 1 illustrates the general electromagnetic source imaging paradigm. Neuronal activity within the brain is modeled as a distribution of dipole currents, denoted by current dipoles ('sources') placed in structures across the brain. The dipole source locations are obtained using anatomic magnetic resonance imaging (MRI). Then, a numerical solution of Maxwell's equations ('forward solution') relates dipole source currents in each brain region to their associated M/EEG measurements. This solution is termed the forward solution, and gives rise to the forward matrix. Then, by incorporating a model of measurement noise, one arrives at a measurement equation. This measurement equation can then be inverted given the M/EEG data to obtain estimates of neuronal source currents across the brain. Thus, this technique is also often referred to as source estimation, source modeling or source localization.

The development of accurate forward solutions that account for brain anatomy and cortical surface geometry, along with significant advances in statistical signal processing, has led to reliable inverse solutions for cortical current distributions. Thus, electromagnetic source imaging is widely used for resolving neuronal dynamics in superficial cortical structures. However, because M/EEG signal amplitudes attenuate steeply with increasing source-sensor distance, it has been challenging to use electromagnetic source imaging for assessing neuronal dynamics in deeper subcortical regions that are farther away from non-invasive M/EEG sensors.

Overall, although existing electrophysiology-based techniques provide excellent temporal resolution, they have limited spatial resolution for activity in deep brain regions. Therefore, there remains a need for improved non-invasive methods and techniques to access and characterize deep brain activity with jointly high temporal and spatial resolution.

SUMMARY OF THE DISCLOSURE

The present disclosure provides methods of electromagnetic source imaging with non-invasive M/EEG recordings and MRI-based anatomic measures that can be used to identify distinct M/EEG field patterns arising from subcortical and cortical structures, and provides a hierarchical subspace pursuit algorithm to estimate neural currents in the subcortical structures. The disclosed algorithms and processes can be used, for example, to non-invasively estimate millisecond-scale dynamics involving subcortical regions, which have critical roles in healthy and abnormal brain function.

In one aspect, the present disclosure provides a method for non-invasively characterizing electrophysiological activity within deep brain regions based on data measurements acquired during a functional task of interest. The method comprises the steps of (a) acquiring data representative of brain activity of a subject during a functional task of interest, (b) acquiring magnetic resonance images of brain anatomy of the subject, (c) using the images to construct hierarchical source spaces in superficial (cortical) and deep (subcortical) regions of the brain, (d) estimating ambient noise, (e) using the hierarchical source spaces to map neural source activity to the measured data, (f) determining the minimum norm source current estimates (MNE) and refining these estimates to sparse subsets within a given hierarchy in the hierarchical source space, and (g) performing the sparse estimation in step f iteratively across the hierarchy of source spaces to identify both a superficial and a deep source whose activity underlies the measured data.

The measured field comprises at least one of an electrophysiologic measurement obtained with electroencephalography (EEG) and magnetoencephalography (MEG). The hierarchical source spaces can be constructed from anatomic MRI, and the spaces include dipoles corresponding to the neocortex, hippocampus, the gray-white matter interface, and in the subcortical volumes.

The step of constructing hierarchical source spaces can comprise (a) grouping clusters of neocortical dipoles and hippocampal dipoles into surface patches, and (b) grouping clusters of subcortical dipoles into volume subdivisions, wherein the patches and the subdivisions each vary in levels of coarseness across the hierarchies. The step of constructing patches and subdivisions can include sizing the patches and subdivisions to homogenize current strengths, and can also include assigning higher resolution to regions with high current densities and lower resolution to regions with low current densities, thereby enabling weaker and stronger gain regions to have comparable consideration in an inverse solution.

In other aspects of the invention, the step of refining the minimum norm estimates to salient sparse subsets can comprise an iterative search for a predetermined number of sources that correlate to the measured data with least residual error. The step of estimating the sparse subset of sources relevant to the measurement across the hierarchy of source spaces can comprise (a) obtaining a first sparse estimate on a coarse brain-wide source space in the hierarchy to identify at least one patch in the source space whose activity correlates to the measured field; (b) obtaining a sparse estimate on at least one patch in a refined source space in the hierarchy having patches that are finer than the source space of step (a) that correlates to the sources from step (a) to identify at least one patch in the refined source space whose activity correlates to the measured field; (c) repeating the process of refinement in step (b) on increasingly finer patches that correlate to the source estimated in step (b) to identify at least one patch in each refined source space whose activity correlates to the measured field, and (d) obtaining a sparse estimates on a composite source space comprising the best estimates of cortical patches from step (c) and the full subcortical source space to select cortical and subcortical brain regions whose activity correlate best to the measured field. A patch can be selected to be correlated with the patch identified as the sparse estimate in the previous step when the patch is at least one of closely located and overlapping.

In another aspect of the disclosure, a method for imaging electromagnetic sources within deep brain structures based on M/EEG data identified while a subject is performing a functional task of interest and anatomical MRI of the brain of the subject employing a sparse inverse identification of the sources of interest is provided. The method can comprise (a) using images of the brain to construct hierarchical source spaces in superficial (cortical) and deep (subcortical) regions of the brain, the hierarchical source spaces comprising at least a first set of patches of the superficial and deep regions of a first preselected level of coarseness, and a second set of patches at a second preselected level of coarseness, each of the patches in each set being sized to homogenize current strengths, (b) mapping neural source activity to the measured fields, (c) estimating noise statistics, (d) computing the minimum norm source current estimates (MNE) and refining these estimates to salient sparse subsets within a selected hierarchy to provide a sparse estimation, and (e) performing the sparse estimation in step d iteratively across the hierarchy of source spaces to identify at least one superficial and at least one deep source whose activity underlies the measured M/EEG data.

The process of constructing patches and subdivisions enables weaker and stronger gain regions to have comparable consideration in an inverse solution, while implicitly assigning higher resolution to regions with high current densities and lower resolution to regions with low current densities. The subspace pursuit process can comprise determining a mutual coherence threshold $\mu$ to enforce incoherence during the subspace pursuit search, and the step of determining the mutual coherence cam comprise determining the maximum correlations between the modes of forward solutions from pairs of neighboring cortical patches.

In another aspect, the present disclosure provides a method for electromagnetic source imaging based on non-invasive M/EEG recordings and MRI-based anatomic measures to employ information within M/EEG field patterns for estimating source currents across superficial and deep brain regions. The method can comprise (a) computing the minimum norm source current estimates (MNE) (b) refining these estimates to identify salient sparse subsets wherein superficial and deep brain regions have distinct field patterns, and (c) performing the sparse estimation in step b iteratively across the hierarchy of source spaces to identify at least one superficial and at least one deep source whose activity underlies the measured M/EEG data. The minimum norm estimate can localizes cortical sources underlying the M/EEG measurements. The method can also comprise the step of acquiring magnetic resonance images of the brain and using the images to construct hierarchical source spaces in the cortical and subcortical regions of the brain.

In another aspect, the hierarchy of sources can comprise at least one of a plurality of cortical source spaces of varying patch sizes, a plurality of subcortical volume subdivisions, and a composite of cortical and subcortical source spaces with varying combinations of regions. The cortical surface patches and subcortical volume subdivisions can be sized to have homogeneous current strengths.

In yet another aspect of the invention, a hierarchical subspace pursuit process for characterizing electrophysiological activity within deep brain regions based on non-invasive M/EEG measurements, the pursuit process being performed on a plurality of hierarchical source spaces, each of the hierarchical source spaces comprising a plurality of surface patches and volume subdivisions representing specific cortical and subcortical regions of the brain is provided. The method includes (i) performing a subspace pursuit on the cortical source space comprising a plurality of coarse patches to identify at least one patch in the source space that correlates to a measured field, (ii) performing a subspace pursuit in a space of patches overlapping the patch identified in step (i) in the cortical space comprising patches of a fine area size to identify at least one patch in the cortical space comprising patches of a fine area size that correlates to the measured field, and (iii) performing subspace pursuit in a composite space comprising the cortical space patches identified in step (ii) and the space of subcortical sources to select cortical and subcortical brain regions whose activity correlate best to the measured field. The patches can be sized to have homogenous current strengths.

These and other aspects of the disclosure will become apparent from the following description. In the description, reference is made to the accompanying drawings which form a part hereof, and in which there is shown a preferred embodiment of the disclosure. Such embodiment does not necessarily represent the full scope of the invention and reference is made therefore, to the claims herein for interpreting the scope.

BRIEF DESCRIPTION OF THE DRAWINGS

FIG. 3C illustrates subcortical volumes comprising subdivided anatomic segmentations. Each subdivision is a different color. The leftmost frame of FIG. 3C is a coronal plane view, the central frame of FIG. 3C is a horizontal plane view, and the rightmost frame of FIG. 3C is a sagittal plane view.

FIGS. 5A-F illustrate an approach to exploit sparsity constraints for the deep brain source imaging problem. In particular, the diagram shows a hierarchical search to identify relevant sparse (and distinguishable) subcortical and cortical sources underlying the measurement. The hierarchical reduction of the full brain source space to relevant sparse distinguishable subsets is achieved as below: (A) the space of all possible sources across the brain. (B) A sparse cortical region most relevant to the measurement under study. (C) Refined sparse cortical regions within and around the region in Panel B. Different colors are used for neighboring patches to highlight patch boundaries. (D) Refined sparse cortical region most relevant to the measurement. (E) Joint source space comprising the sparse cortical region and subcortical volumes. The sparse subset of the cortical source space allows subcortical areas to show through in the inverse solution. It is possible to search across these sparse and therefore distinguishable sets of sources to localize appropriate subcortical and cortical sources. (F) Final sparse cortical and subcortical regions most relevant to the measurement under study.

FIGS. 8A-F illustrate cortical and subcortical estimates for the auditory brainstem recordings of FIG. 7. Estimates are obtained with the proposed sparse hierarchical deep brain imaging algorithm. (A) Reduced cortical source space obtained as a result of initial source space reduction performed upon the middle latency recordings. Estimates shown on the inflated surface are snapshots at 25 msec and thus comprise patches in primary auditory areas. Subspace pursuit (SP) and minimum norm estimation (MNE) algorithms were then applied on the reduced source space, to localize sources of the auditory brainstem recordings. The leftmost frame of FIG. 8A is a first view of the reduced cortical source space, the central frame of FIG. 8A is a second view of the reduced cortical source space, and the rightmost frame of FIG. 8A is a third view of the reduced cortical source space. (B-C) Representative MRI maps showing snapshots of subspace pursuit and MNE estimates at 5 msec (around appearance of wave V). MRI slice locations in the surface right-anterior-superior (RAS) coordinate system are 115 mm (coronal for the leftmost frame of FIGS. 8B and 8C), 126 mm (horizontal for the central frame of FIGS. 8B and 8C) and 142 mm (sagittal for the leftmost frame of FIGS. 8B and 8C). (D) Summary of mean activity by anatomic region for each estimation algorithm. Legend: cortical (co), putamen (r/lp), caudate (r/lc), thalamus (r/lt), hippocampus (r/lh), lateral geniculate (r/ll), medial geniculate (r/lm), and inferior colliculus (ic), where r/l refer to right/left. (E-F) Time courses of source current estimates obtained with SP and MNE algorithms. (D-F) SP estimates indicate wave V arises from focal sources in the inferior colliculus—as in established literature. SP is more specific to the inferior colliculus than MNE. All estimates displayed are resultants across dipoles within their respective patch or volume subdivisions. Each time course shown corresponds to a selected subdivision in the respective anatomic regions indicated in legends.

DETAILED DESCRIPTION OF THE DISCLOSURE

The present disclosure describes methods of electromagnetic source imaging with non-invasive M/EEG recordings and MRI-based anatomic measures that can be used to acquire gain-insensitive information in M/EEG arising from subcortical and cortical structures, and provides a hierarchical subspace pursuit algorithm to estimate neural currents in the subcortical structures. Distinctions between field patterns can be used to localize subcortical sources and distinguish subcortical versus cortical contributions using the hierarchical subspace pursuit process or algorithm.

Figure 2:
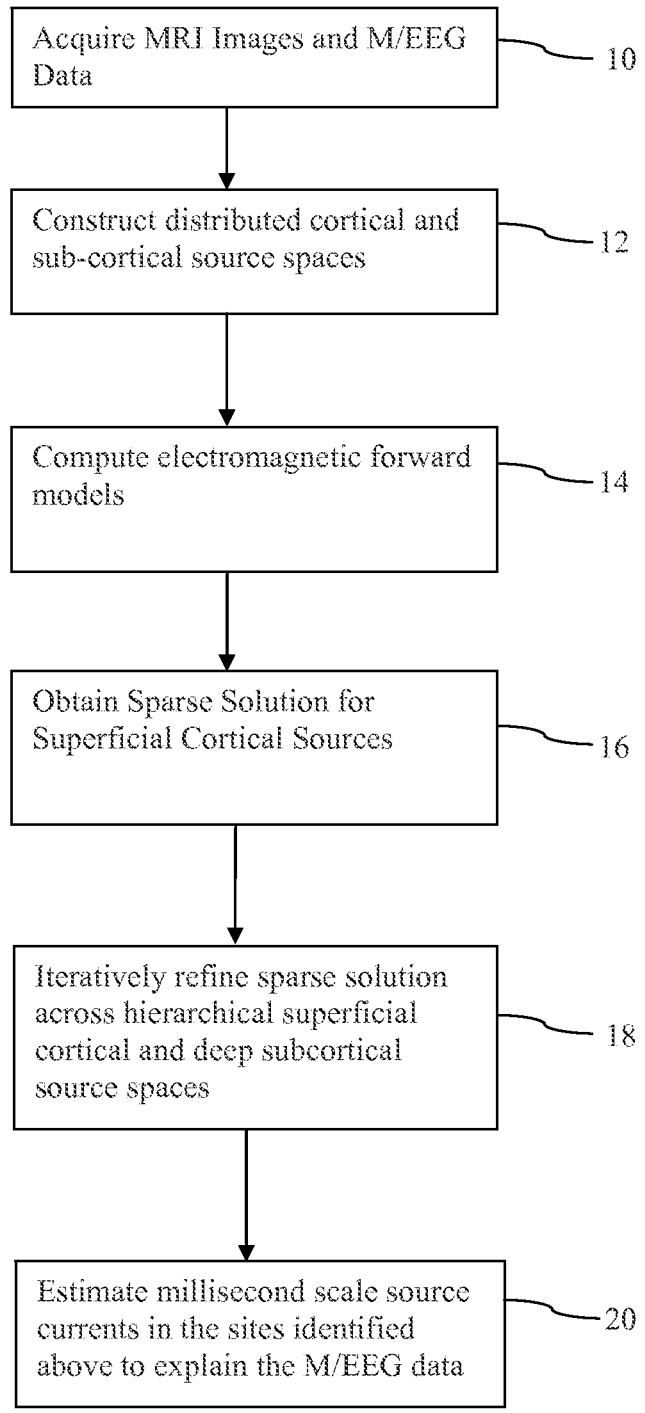
FIG. 2 is a flow chart illustrating the general series of steps for deep brain electromagnetic source imaging using M/EEG recordings and anatomical MRI.

Referring now to FIG. 2, a flowchart illustrates a series of steps for estimating source currents from deep brain regions with a hierarchical subspace pursuit algorithm. Initially, M/EEG data are acquired during a neurophysiologic paradigm of interest. These recordings are complemented with magnetic resonance images of the subject's brain anatomy (step 10). Next, distributed source spaces are constructed from the images (step 12) and electromagnetic forward solutions G are computed using Maxwell's equations (step 14). Analysis of these forward solutions reveals that a sparse inverse solution would enable distinctions between cortical and subcortical sources of electromagnetic fields recorded with M/EEG. Therefore, we disclose a sparse hierarchical inverse solution for deep brain electromagnetic source imaging. In sequence, this involves computation of the minimum norm estimates (MNE, step 16), refinement of these estimates with a subspace pursuit scheme (step 18) and iterative evaluation of the MNE+subspace pursuit procedure across hierarchies of cortical and subcortical source spaces. This iterative process enables identification of both superficial and deep locations of brain activity, and allows estimation of the source currents therein (step 20). Each of these steps is described more fully below.

Acquire Images

Figure 3A:
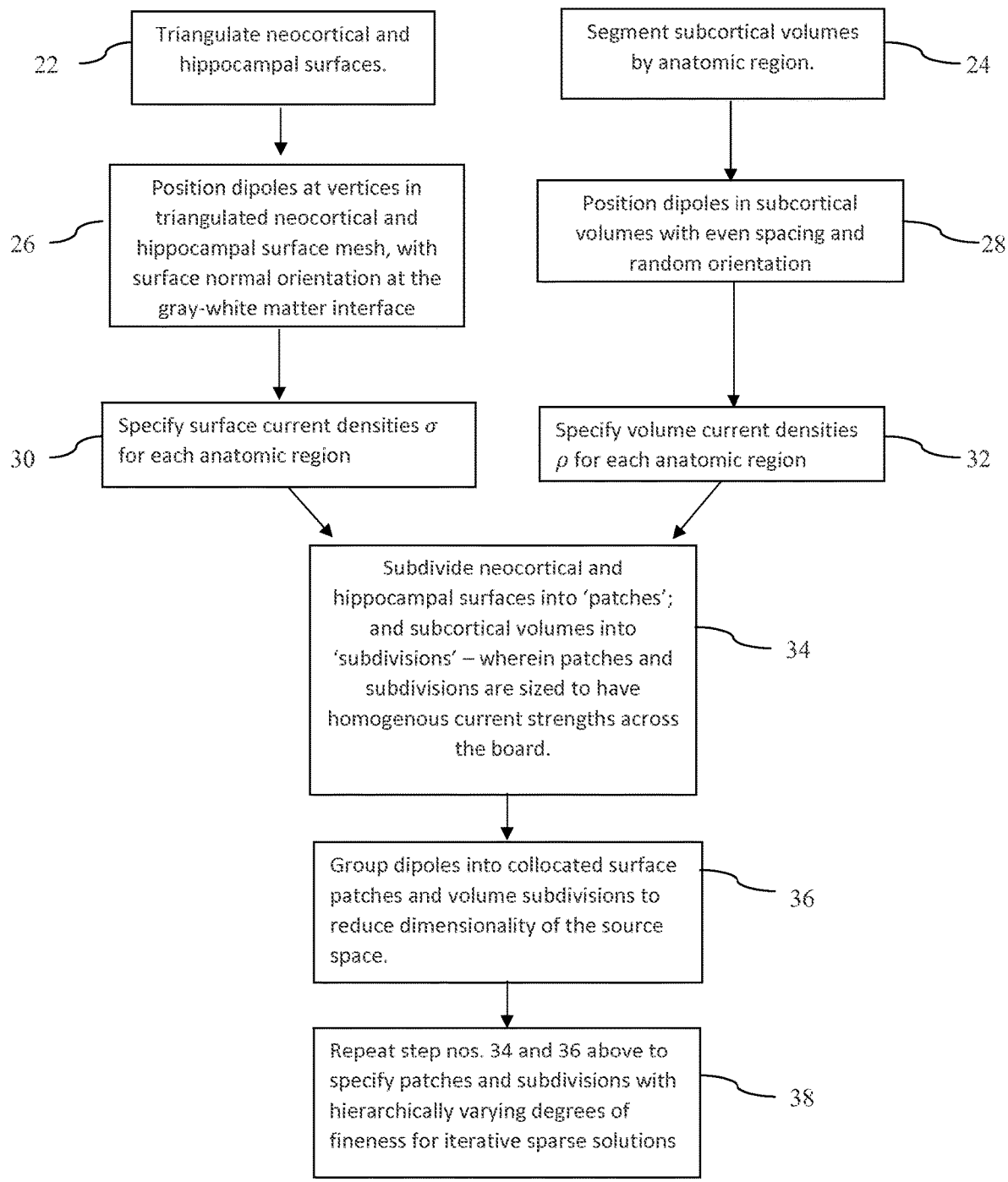
FIG. 3A is a flow chart illustrating the steps for defining cortical and subcortical source spaces.

Referring still to FIG. 2, and now also to FIG. 3A, after the magnetic resonance images are acquired, distributed neural source spaces are constructed (step 12). Image analysis software can be used to reconstruct and triangulate neocortical and hippocampal surfaces (step 22), as well as to segment the subcortical volumes by anatomic region (step 24). Subsequently, dipoles are positioned at vertices in the triangulated surface mesh for neocortex and hippocampus, at the gray-white matter interface, and assigned orientations fixed normal to the neocortical and hippocampal surfaces respectively (step 26). The neocortical and hippocampal dipole placements are performed consistently as both structures have a similar layered cyto-architecture, and as the hippocampal inner structure is not accessible with anatomical MRI. Dipoles are also placed in subcortical volumes (thalamus, caudate, putamen, amygdala, medial and lateral geniculate nuclei, brainstem) extracted from the segmentations, as well as in specific smaller nuclei (medial and lateral geniculate) defined based on standard anatomic landmarks and segmentations. (step 28) Although other configurations are possible, the dipoles can be positioned at a 1 mm voxel spacing, and oriented randomly. Although a number of different segmentation software packages could be used, the FreeSurfer Software Suite available at freesurfer.net has been used in exemplary applications. Other suitable software packages could include the brainVISA/Anatomist package (brainvisa.info) and the FMRIB Software Library (fsl.fmrib.ox.ac.uk/fsl/fslwiki).

Construct Source Spaces

Referring still to FIG. 2, and now also to FIG. 3A, after the magnetic resonance images are acquired, distributed neural source spaces are constructed (step 12). Image analysis software can be used to reconstruct and triangulate neocortical and hippocampal surfaces (step 22), as well as to segment the subcortical volumes by anatomic region (step 24). Subsequently, dipoles are positioned at vertices in the triangulated surface mesh for neocortex and hippocampus, at the gray-white matter interface, and assigned orientations fixed normal to the neocortical and hippocampal surfaces respectively (step 26). The neocortical and hippocampal dipole placements are performed consistently as both structures have a similar layered cyto-architecture, and as the hippocampal inner structure is not accessible with anatomical MRI. Dipoles are also placed in subcortical volumes (thalamus, caudate, putamen, amygdala, medial and lateral geniculate nuclei, brainstem) extracted from the segmentations, as well as in specific smaller nuclei (medial and lateral geniculate) defined based on standard anatomic landmarks and segmentations. (step 28) Although other configurations are possible, the dipoles can be positioned at a 1 mm voxel spacing, and oriented randomly. Although a number of different segmentation software packages could be used, the FreeSurfer Software Suite available at http://freesurfer.net/ has been used in exemplary applications. Other suitable software packages could include the brainVISA/Anatomist package (http://brainvisa.info/) and the FMRIB Software Library (http://fsl.fmrib.ox.ac.uk/fsl/fslwiki/).

To reduce the dimensionality of the inverse problem, and make it better posed for the number of sensors typically available in M/EEG recordings, the dipoles are grouped into "surface patches" for neocortex and hippocampus, and "volume subdivisions" for subcortical volumes (steps 30, 32, 34, 36). This process does not cause loss of information as small groups of nearby dipole clusters generate similar or correlated electromagnetic fields at the external sensors. The process for grouping dipoles into patches and subdivisions is described below.

First, cortical and hippocampal dipoles are grouped into patches. This can be accomplished within the MNE software package available at martinos.org/mne/stable/index. In one example, the cortical and hippocampal surfaces were each approximated with the topology of recursively subdivided icosahedra, i.e., with a solid figure with twenty plane faces. For each icosahedron subdivision, detailed surface geometry information were used to derive "surface patches".

Second, subcortical dipoles are grouped into "volume subdivisions" obtained by subdividing the anatomic subcortical segmentations derived from the FreeSurfer Software Suite. In particular, the volume subdivisions are sized to homogenize current strengths within dipole groups across the brain. In one example, the volume subdivisions were sized to homogenize current strengths across cortical and subcortical regions as follows. The surface current densities $\sigma$, and volume current densities $\rho$, were specified across brain regions in a structure-specific manner (steps 30, 32). Using neocortical surface current density $\sigma$ and average cortical patch area $\overline{A}$, the average current strength for cortical patches was computed as $\sigma\overline{A}$. Next, total volumes V for anatomically distinct subcortical regions were computed. Then, the number of subdivisions for a given subcortical volume segmentation was derived as $\eta = \rho V / \sigma \overline{A}$. Finally, using a k-means based clustering algorithm, the dipoles within the anatomical region are grouped into n distinct equally sized clusters. The typical volume of a subcortical subdivision can range 150-800 mm$^3$, depending on structure.

The process of homogenizing current strengths enables weaker and stronger gain regions to have comparable consideration in an inverse solution, while implicitly assigning higher resolution (finer subdivisions) to regions with high current densities and lower resolution (larger subdivisions)

to regions with low current densities. While the above-mentioned methods detail one way for sizing the surface patches and volume subdivisions to homogenize current strengths across sources, several other decomposition methods can be used.

Figure 3B:
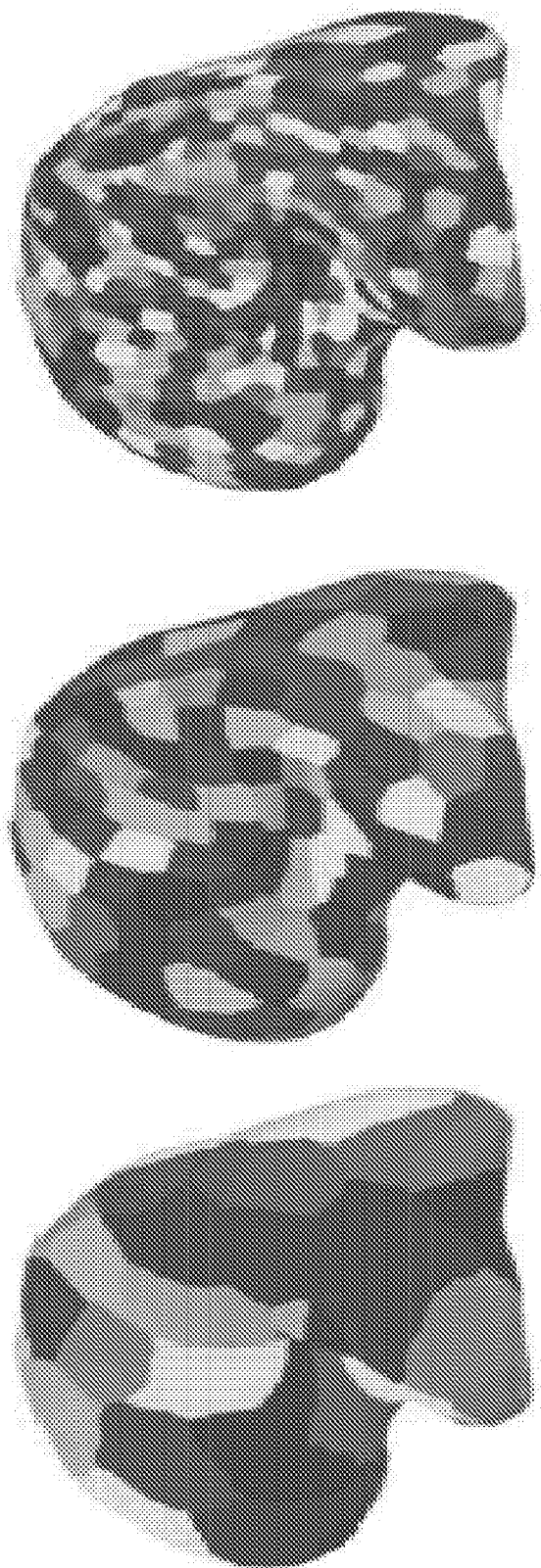
FIG. 3B illustrates a series of cortical surfaces divided into patches of varying sizes. Each patch is a different color. The leftmost frame of FIG. 3B includes a cortical surface divided into patches of a first size, the central frame of FIG. 3B includes a cortical surface divided into patches of a second size, and the leftmost frame of FIG. 3B includes a cortical surface divided into patches of a third size.

Referring again to FIG. 3A (step 38), and now also to FIG. 3B-3C, example cortical and subcortical source spaces resulting from the above source space construction techniques are illustrated. In FIG. 3B, cortical patches with three different sizes (varying coarseness) for use in a hierarchical inverse solution are shown. The set of coarse patches has an average area 2500 mm$^2$ (on left) and is denoted $\mathbb{C}^{(1)}$, the set of finer patches with average area 650 mm$^3$ (middle) is denoted $\mathbb{C}^{(2)}$, and the set of even finer patches with average area 175 mm$^2$ (right) is denoted $\mathbb{C}^{(3)}$. In FIG. 3C, a subcortical source space S comprising volume subdivisions across caudate, putamen, hippocampus, amygdala, thalamus, lateral and medial geniculate nuclei, and brainstem is shown. These subdivisions have volume ranging 150-800 mm$^3$ and are illustrated in different planes of view (coronal, horizontal and sagittal).

Compute Forward Solutions

Figure 1:
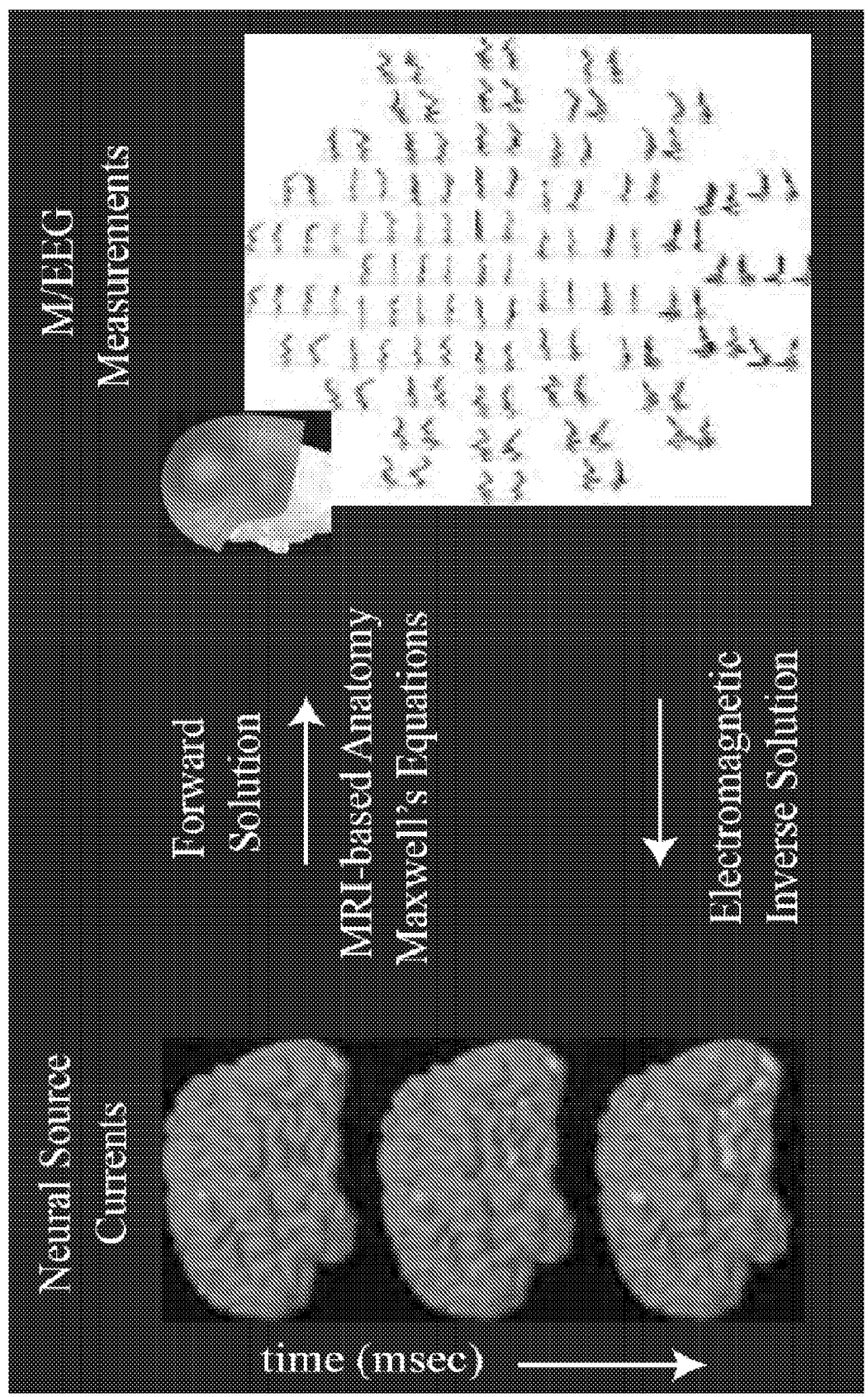
FIG. 1 is a functional diagram illustrating electromagnetic source imaging with M/EEG and anatomical MRI.

Referring again to FIGS. 1 and 2, in step 14, it is possible to calculate a series of electromagnetic forward solutions for each source in the above source space. For a given source (surface patch or volume subdivision) of known location, Maxwell's equations determine the mapping between source activity and electromagnetic fields at the sensors i.e., the electromagnetic forward solution G. Then, activity in dipoles located within a given source region, denoted by source currents X, generates a vector y of field patterns at the M/EEG sensors as below:

$$y_{N\times 1} = G_{N\times M} X_{M\times 1}$$

where N is the number of sensors and M is the number of dipole sources in the region of interest. The mapping specified in G is linear as it arises from a quasi-static approximation to Maxwell's equations.

In an exemplary M/EEG application, a Neuromag Vectorview™ MEG system (Elekta Neuromag, Helsinki, Finland) comprising 306 sensors across 102 sensor locations (2 planar gradiometers and 1 magnetometer per location) and a standard 70-lead EEG electrode configuration were used to calculate the forward solutions. To ensure alignment between the brain source coordinates and sensor coordinates used for forward solutions, the positions of M/EEG sensors and corresponding fiduciary points were digitally co-registered with the MRI data acquired for source space construction (step 10). For each regional subdivision in the source space, MEG and EEG forward solutions were generated within the MNE software package, using a three-compartment boundary element model derived from the MRI data. Dipoles within 5 mm of the inner skull bounding surface were excluded to avoid numerical errors. To account for non-homogeneity between the current densities across regions in the brain, the G for each region was multiplied by regional current strength denoted as c. For each subcortical region, current strength was derived as c=ρV where ρ and V are the regional current density and volume respectively. For each neocortical and hippocampal patch, current strength was derived as c=σA where σ and A are the surface current density and area respectively.

For any subdivision in the source space, the columns of G obtained above represent fields arising from small collections of neighboring dipoles, and thus are highly correlated. Thus, information in the forward solutions for individual regions can be condensed into a low-dimensional approximation i.e., into a low-rank basis derived using a reduced singular value decomposition $$G = U_{N\times B} S_{B\times B} W_{B\times M}$$

$$\hat{G} = U_{N\times P} S_{P\times P}$$

where P<B is the number of eigen-modes retained in the low-rank approximation. For each subdivision, P is chosen such that the reduced order $\hat{G}$ represents at least 95% of the total spectral energy in G:

$$\frac{\sum_{b=1}^{P} S_{bb}}{\sum_{b=1}^{B} S_{bb}} \geq 0.95.$$

Typically P=2-6 modes are sufficient to capture 95% of the spectral energy in G. This approach (a) enables reduction of the dimensionality of G, (b) minimizes representation error on average, and (c) implicitly defines reduced subspaces for regional forward solutions for use in inverse solutions. All following analyses use these low-rank approximations of the forward models.

Analyze Forward Solutions to Motivate Inverse Approach

The eigenmodes in $\hat{G}$ represent normalized field patterns that can arise from some distribution of source activity in a region of interest. To understand how to distinguish subcortical and cortical contributions to M/EEG data within an inverse solution, it is useful to compare field patterns arising from subcortical vs. cortical activity. These comparisons can be quantified using metrics such as principal angles which are established metrics for subspace comparisons.

Principal angles between subspaces of possible field patterns from regions i and j, defined by the reduced order electromagnetic forward models $\hat{G}_i$ and $\hat{G}_j$ respectively, are denoted $\Theta_{i,j}$. The angles can be computed using a formulation that uses the singular value decomposition:

$$\hat{G}'_i \hat{G}_j = U p_{i,j} \sum_{i,j} W p_{i,j},$$

$$\sum_{i,j} = \text{diag}(s_1, s_2, \ldots s_n)$$

$$= \text{diag}(\cos\theta_1, \cos\theta_2, \ldots \cos\theta_n)$$

$$\Theta_{i,j} = [\theta_1, \theta_2 \ldots \theta_n].$$

Figures 4A, 4B:
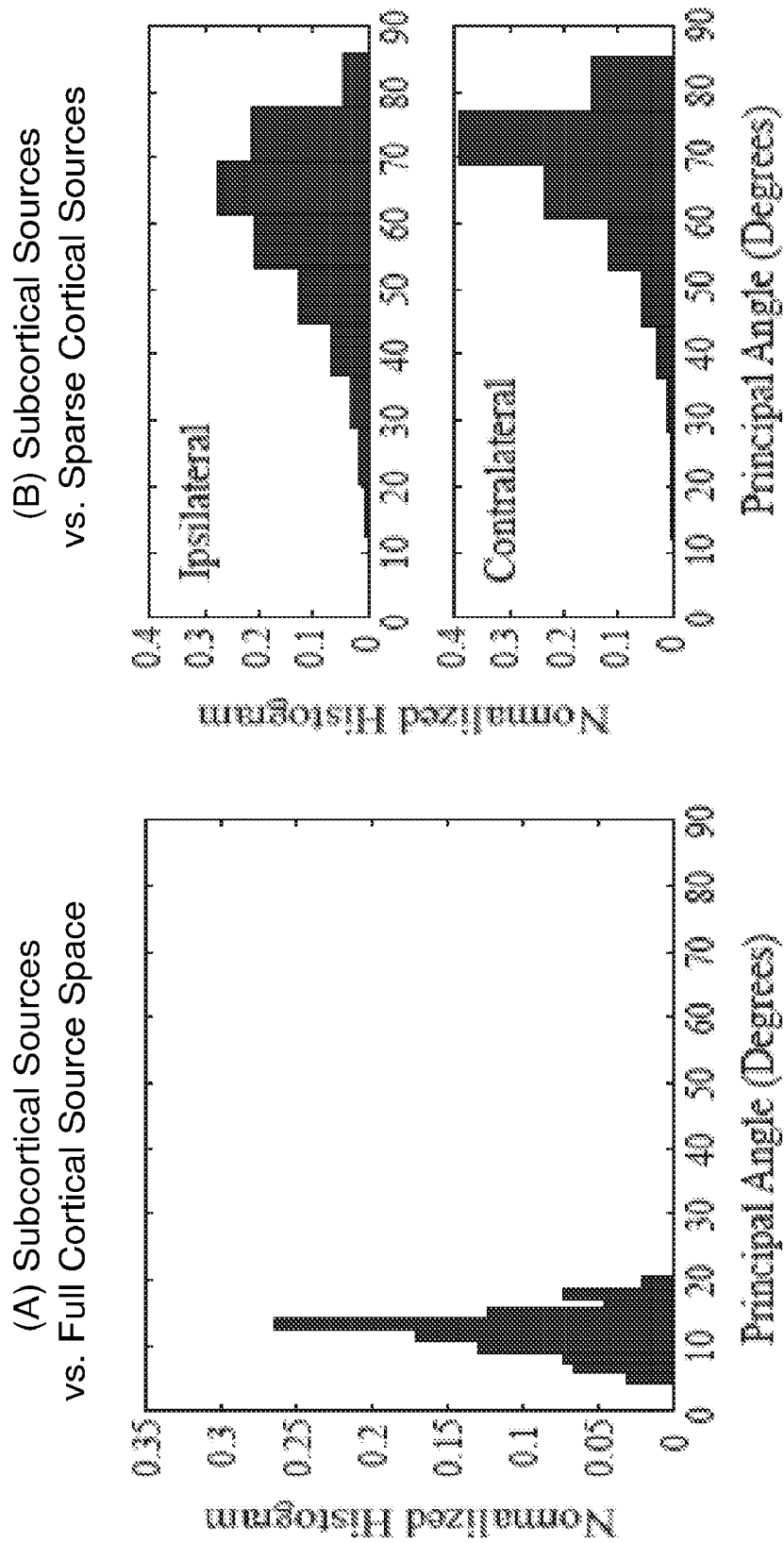
FIGS. 4A-D illustrate that sparsity constraints enable distinctions between deep subcortical and superficial cortical contributions to M/EEG field patterns. Each panel contains histograms of principal angles between MEG field patterns generated by activity in pairs of brain regions. The principal angles quantify distinctions between subspaces defining field patterns from the two regions (0 degree indicates identical, and 90 degree indicates fully orthogonal). (A vs. B) Full cortical source space can generate most any field pattern that a subcortical source space can, while sparse cortical sources cannot. (B vs. C) Sparse subcortical and cortical source spaces generate field patterns that are just as distinct as those generated by pairs of sparse cortical source spaces. (C vs. D) Pairs of subcortical regions also generate distinct field patterns, like pairs of cortical regions, but exhibit a bit more overlap due to their greater distance from sensors. (B-D) A large proportion of the principal angles are high and close to orthogonal when sparse regions are compared.
Figure 4D:
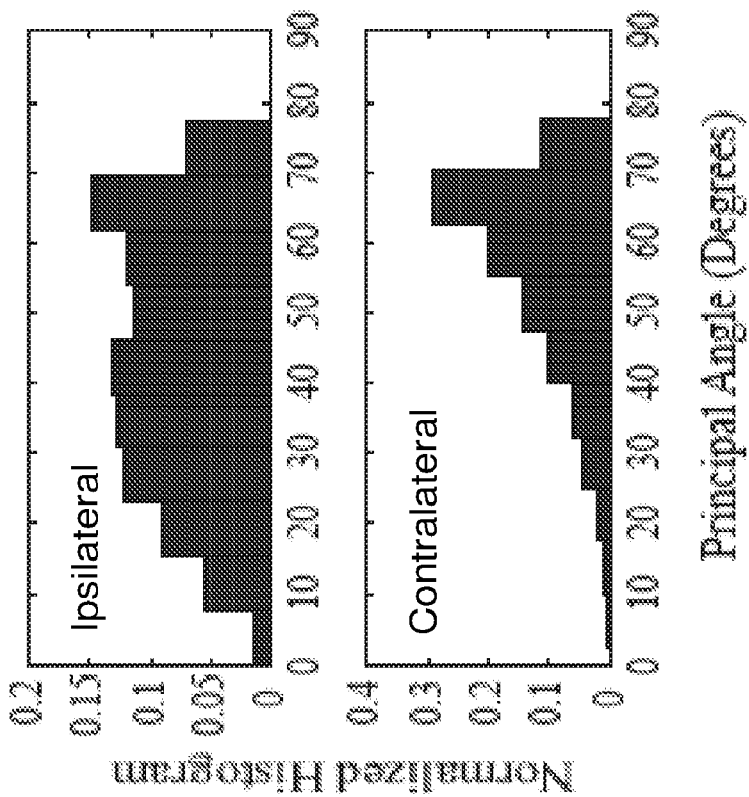
Figure 4C:
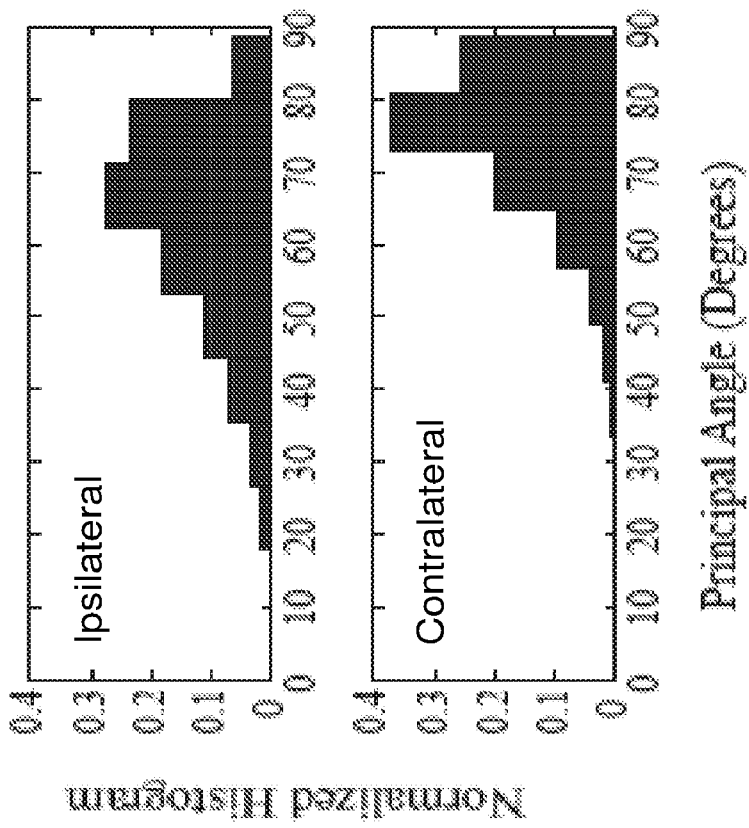

FIG. 4A shows the principal angles between field patterns arising from activity in the subcortical regional subdivisions and the full cortical source space respectively. The low angles illustrate that the full cortical source space can explain most field patterns arising from a subcortical subdivision. This is because the full cortical case has several eigen-modes spanning most possible field patterns including those generated by activity within a subcortical volume subdivision. FIG. 4B illustrates angles between field patterns from sparse subcortical and cortical regions, which are significantly higher than those in FIG. 4A, illustrating near orthogonality between field patterns generated by sparse pairs of regions. FIG. 4C illustrates that pairs of cortical regions also give rise to near orthogonal field patterns. The angle trends in FIG. 4B-4C are similar, illustrating that subcortical and cortical sources can be distinguished using differences between their respective field patterns. FIG. 4D illustrates field patterns arising from pairs of subcortical regions, and shows similar trends to FIG. 4C. Therefore, in every case where sparse regions are compared, the field patterns are more distinguishable than the full cortical space case of FIG. 4A.

A Sparse Inverse Solution for Deep Brain Electromagnetic Source Imaging

The above results demonstrate the key idea that sparsity constraints within an inverse solution can enable robust distinctions between subcortical and cortical contributions to M/EEG data (field patterns). Furthermore, sparsity constraints are suitable in a variety of neurophysiologic scenarios as only a small proportion of the brain has salient activity in many cognitive experiments and clinical conditions. These observations motivate a sparse inverse solution for the deep brain electromagnetic source imaging problem.

One such sparse inverse solution is outlined in FIG. 2, steps 16, 18 and 20. The approach is to hierarchically reduce the space of all possible sources to sparse subsets most relevant to a given M/EEG recording. The electromagnetic inverse problem and steps in the hierarchical iterative sparse solution are described formally below.

The electromagnetic inverse problem is: to estimate the source currents X underlying M/EEG measurements Y, given the electromagnetic forward solution G linking the two:

$$Y_{N \times T} = G_{N \times M} X_{M \times T} + V_{N \times T}$$

Here, the observation noise V is assumed to be Gaussian, temporally uncorrelated, and specified completely by spatial covariance $Q_{N \times N}$ independent of X, N is the number of sensors, M is the number of dipole sources across the brain, and T is the number of time points in the measurement.

For a distributed source space comprising K regions across the brain, columns of G and rows of X can be grouped by region and the measurement equation can be rewritten as:

$$Y_{N \times T} = [G_1, G_2, \ldots, G_K] \begin{bmatrix} x_1 \\ x_2 \\ \vdots \\ x_k \end{bmatrix} + V_{N \times T}$$

where the set of regions (patches or subdivisions) is [1, 2, ..., K], $G_k$ is the electromagnetic forward solution for the $k^{th}$ region, and $x_k$ denotes the source current of dipoles in the $k^{th}$ region across time. Thus, the norm of $x_k$ can be thought of as the quantum of activity from the $k^{th}$ region, and indicate the least squares match between the possible field patterns from a region and field patterns within the M/EEG data.

Compute MNE Estimates:

The classic solution for this problem is given by the minimum $l_2$-norm estimate (MNE) which projects measurement Y onto the range of G while accounting for noise characteristics and prior information. The MNE solution for source currents X given full forward solution G, M/EEG measurements Y, noise statistics Q and prior covariance R on source currents is given by:

$$x^{MNE}(Y,G,Q,R) = RG'(GRG'+Q)^{-1}Y$$

However, the above-mentioned principal angle results suggest that a simple application of MNE on the full brain source space, with G specifying the composite forward solution for all subcortical and cortical sources, will likely localize to the cortical source spaces even if the activity arises from a deeper subcortical source. Instead, as distinctions in subcortical and cortical field patterns arise when sparse source spaces are considered, localizing subcortical contributions requires refining the MNE estimates. An ideal inverse algorithm would have the ability to refine the classical MNE solution in two ways: (a) reduce the full distributed source space to accurate sparse cortical subsets alongside deep sources, and (b) concentrate the source current estimates into the appropriate subcortical sources.

Refine MNE Estimates with Subspace Pursuit:

Both of the above objectives are served well by projection pursuit methods, which identify sparse projections to best explain multivariate data. First, pursuit methods can find sparse cortical regions most relevant to the measured fields, amidst the high-dimensional dictionary of all regions and their corresponding field patterns. This is because they deal uniquely well with the curse of dimensionality. Second, upon identifying the sparse cortical contributors, the pursuit search can be repeated in the reduced source space to search for weak but distinct subcortical contributors. This is because pursuit methods are robust to noise and outliers, and can recover small amplitude features in large dictionaries. These methods can be implemented with subspace pursuit algorithms, which find a sparse projection matching a given dictionary (e.g. matching in the least squares or MNE sense), remove the component along that projection and iterate to find new projections, till all matching projections have been found.

Formally, the subspace pursuit (SP) estimate is written as:

$$[H, \hat{X}_H] = SP(Y, G, Q, R)$$

where H is a set of indices denoting the subset of regions deemed to be most relevant to the measurement. Implicitly H gives a subset of regions whose normalized field patterns match those in the measurement after compensating for noise, and $\hat{X}_H$ specifies source current estimates that can together generate these different field patterns to quantitatively explain measurement amplitudes.

Intuitively, this approach starts with the MNE estimate, iteratively picks out the "relevant" sparse components of the MNE estimate, and refines the MNE estimate until all "relevant" projections have been found.

The above MNE+pursuit process is repeated and adapted across hierarchies of cortical and subcortical source spaces, so as to focus the estimate iteratively into the relevant regions (iteratively reduce the source space to the solution) for greater spatial resolution and accuracy. FIGS. 5A-F illustrates one instance of such a hierarchical source space reduction procedure. Starting from a naïve space of all possible sources (FIG. 5A), it is possible to find a sparse cortical solution (FIG. 5B), perform a finer search in the neighborhood of this sparse cortical solution (FIG. 5C), obtain a refined sparse cortical solution (FIG. 5D). The sparse cortical solution is distinguishable from subcortical sources in general. Then, the search can be repeated with a combination of the reduced/sparse cortical space and the full subcortical space (FIG. 5E) to identify relevant subcortical and cortical sources (FIG. 5F). This iterative process enables identification of both superficial and deep locations of brain activity, and allows estimation of the source currents therein (FIG. 2, step 20).

Formally, if the algorithm starts with a source space $C^{(1)}$, with forward model denoted as $G^{(1)}$, MNE+subspace pursuit is performed to pick L regions that can best explain measured fields:

$$[H_1, \hat{X}_{H_1}] = SP(Y, G^{(1)}, Q, R, L)$$

where $H_1$ denotes the chosen set of L regions in $C^{(1)}$ (FIG. 5B) and $\hat{X}_{H_1}$ denotes the source current estimates in these chosen cortical regions. Next, we repeat the estimation in a finer cortical source space $C^{(2)}$—with patches overlapping $H_2$ and their nearest neighbors (FIG. 5C). The forward model for these patches is denoted as $G^{(2)}$ and we perform subspace pursuit to pick L regions that can best explain measured fields:

$$[H_2, \hat{X}_{H_2}] = SP(Y, G^{(2)}, Q, R, L)$$

where $H_2$ denotes the chosen set of L regions in $C^{(2)}$ (FIG. 5D) and $\hat{X}_{H_2}$ denotes the source current estimates in these chosen regions. This systematic reduction of possible cortical sources can be repeated to the level of fineness relevant to cortical activity in the task under study. This hierarchical reduction process results in a highly spatially resolved subset of relevant sparse cortical sources, denoted as $\mathbb{C}_{(sp)}$ (e.g. as in FIG. 5D). Then, in the final stage search, the subcortical source space S, containing volume subdivisions of caudate, putamen, hippocampus, amygdala, thalamus, lateral and medial geniculate nuclei, brainstem, is considered alongside the sparse cortical source space $\mathbb{C}_{(sp)}$ (FIG. 5E). We denote the composite or joint source space as $J=[\mathbb{C}_{(sp)}, S]$. The forward model for J denoted as $G_J=[\mathbb{C}_{sp}, G_S]$, implicitly contains nearly decorrelated columns, and we perform subspace pursuit to pick L regions that can best explain measured fields:

$$[H_J, \hat{X}_{H_J}] = SP(Y, G_J, Q, R, L)$$

where $H_J$ specifies the set of chosen regions whose dipole activity best explains the data (e.g. as in FIG. 5F), while $\hat{X}_{H_J}$ gives the source current estimates in these subdivisions. We denote these dipole currents as $\hat{x}$ for notational convenience.

Figure 6:
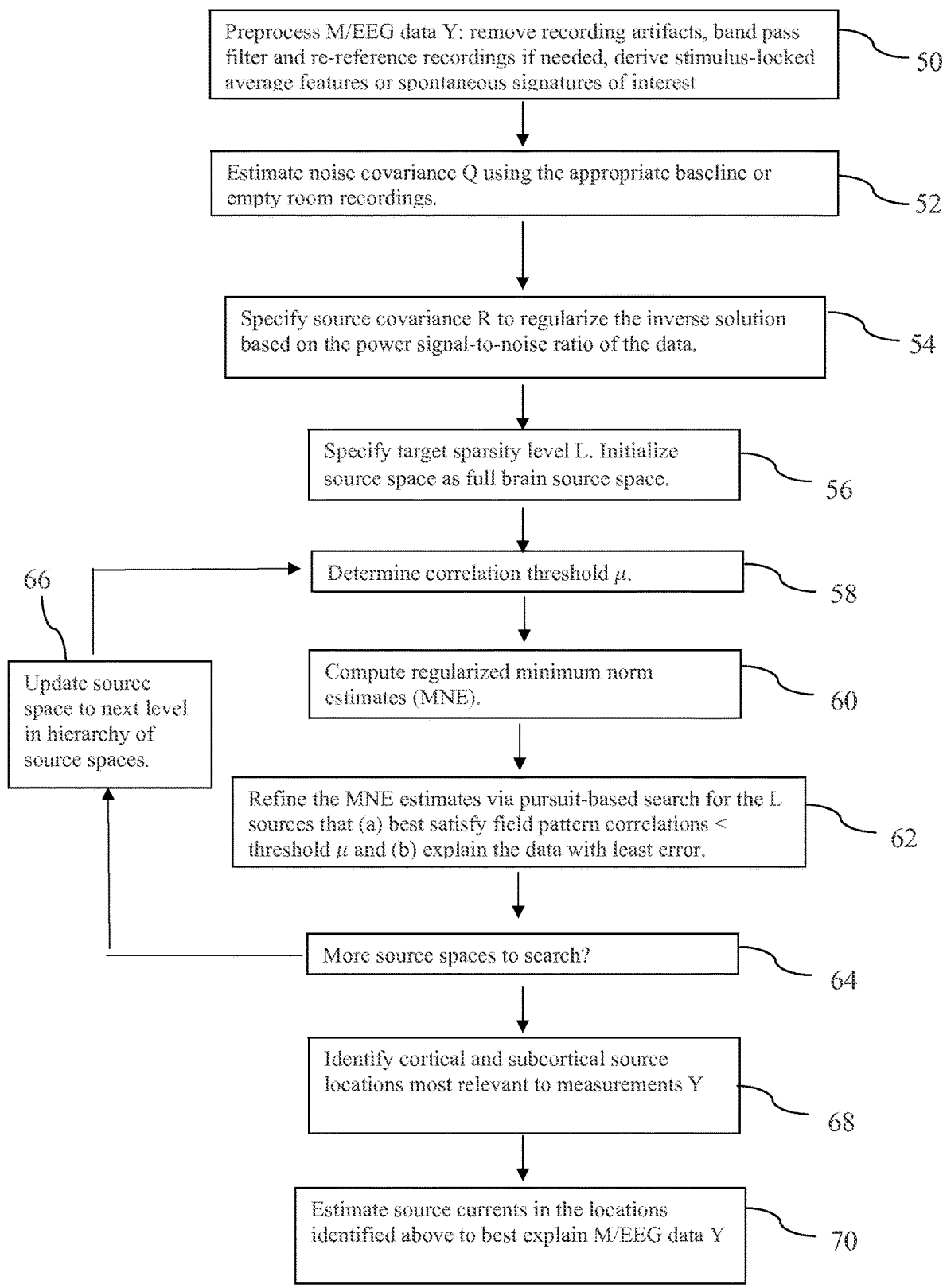
FIG. 6 illustrates a hierarchical subspace pursuit algorithm for deep brain source imaging—in accordance with the approach disclosed above—in simplified flow chart form.

Hierarchical Subspace Pursuit-Based Algorithm for Deep Brain Electromagnetic Source Imaging Referring now to the flowchart in FIG. 6, the algorithm is illustrated in a stepwise manner. Steps 50, 52 and 54 describe the preprocessing of the M/EEG data and estimation of the noise covariance Q and source covariance R. Then in step 56, the target sparsity level L and the starting source space are initialized. Following this, an iterative process is entered. In step 58, the correlation threshold $\mu$ is calculated. Then, the MNE estimates are obtained (step 60) and reduced via subspace pursuit to the L sources that best explain the data while satisfying the correlation threshold (step 62). If there are additional source spaces to search within the hierarchy (step 64), the search space is updated (step 66) and steps 58-62 are repeated. The repetitions are performed until all of the hierarchical source spaces have been searched. The cortical and subcortical source locations most relevant to the measurement are then identified (step 68), and the neural source currents in these locations that explain the M/EEG data are estimated. We further detail the steps within the iterations below.

The mutual coherence thresholds $\mu$, described above, are used in the subspace pursuit algorithm to enforce incoherence during search. To estimate these thresholds, the maximum correlations between the modes of forward solutions from pairs of neighboring subdivisions (e.g., neighboring patches or nearby volumes within an anatomic region) can be computed. These can be averaged within a neighborhood to obtain the average neighborhood maximum correlation, and then across neighborhoods to obtain the threshold $\mu$. In essence, these thresholds ensure that at each iterative subspace pursuit stage, correlation between the current support and new regions entering the solution is $<\mu$, preventing new regions from clustering around neighbors of the current support. Rather, it enforces that new regions entering the solution explain substantially different field patterns than the current support and its neighbors can. For a given subject, one threshold was set for each cortical patch decomposition $\mathbb{C}^{(1)}$, $\mathbb{C}^{(2)}$, and $\mathbb{C}^{(3)}$, and used for the successive hierarchies during cortical source space reduction. The final joint cortical and subcortical estimation stage used the minimum of the threshold from the last cortical stage and the group of subcortical volumes. This allows any of the cortical sources in reduced source space $\mathbb{C}_{(sp)}$ to enter the final solution. Beyond this, the exact value of the threshold does not matter at the final stage because the sparse subcortical and cortical field patterns are implicitly nearly orthogonal.

The MNE Estimates:

As MNE is an established source imaging technique, it can be computed with known procedures. Specifically, the estimated noise covariance Q is eigen-decomposed to $Q=U_Q\Lambda_Q^2 U'_Q$. Then, the measurement equation is whitened by premultiplying with $Q^{-1/2}=\Lambda_Q^{-1}U'_Q$. This gives the whitened measurement $\tilde{Y}=Q^{-1/2}Y$ and whitened forward model $\tilde{G}=Q^{-1/2}G$. Then, a computationally stable rewrite of the MNE estimate is:

$$\hat{X}^{MNE}(\tilde{Y}, \tilde{G}, R) = R\tilde{G}'(\tilde{G}R\tilde{G}' + I_N)^{-1}\tilde{Y}$$

where N is the number of sensors. Computing these current estimates requires specification of the prior covariance matrix R. In practice, R is unknown, and is usually written in terms of a regularization parameter as $\tilde{R}=R/\lambda^2$, giving:

$$\hat{X}^{MNE}(\tilde{Y}, \tilde{G}, \tilde{R}) = \tilde{R}\tilde{G}'(\tilde{G}\tilde{R}\tilde{G}' + \lambda^2 I_N)^{-1}\tilde{Y}$$

Given the SNR of the data, we set $\lambda^2=1/SNR$ and assume $\tilde{R}$ is diagonal. This gives a convenient choice for the elements of $\tilde{R}$:

$$\tilde{R}_{ii} = \frac{TR(I_N)}{TR(\tilde{G}\tilde{G}')}$$

where TR refers to trace of the matrix in brackets. Intuitively, high SNR values enforce source current amplitudes to explain peaks in the data better than the noise. By contrast, low SNR values weight the source covariance more and allow larger discrepancy between measured and predicted data. Standard settings of SNR in the range of 9-25 were used for MEG evoked response recordings where the goal is to capture peaks better than background noise. For EEG recordings, as forward solutions have greater blurring due to the relatively low conductivity of the scalp and skull, greater information is contained in background below peaks, and thus SNR was set to 1. The same SNR value was used through the source space hierarchies.

The subspace pursuit algorithm used to refine and identify a sparse subset of MNE estimates for a given source space is denoted as SP (Y, G, Q, R, L)⇔ SP (Ỹ, G̃, R̃, L), and is performed as follows:

Initialization:
1. Correlation threshold: Compute a correlation threshold $\mu$ mutual coherence) specifying the degree of orthogonality required amongst the selected columns of G̃. This is set as the average worst case correlation between the forward solutions of neighboring cortical patches in the source space under consideration.
2. Support: Compute the standard MNE estimates $\hat{X}^{MNE}$ (Ỹ, G̃, R̃,) as specified, and the $l_{2-norms}$ across time for each row of $\hat{X}^{MNE}$. Specify initial support $H^{(0)}$ as the set of L rows in $\hat{X}^{MNE}$ with largest $l_{2-norms}$ satisfying the degree of orthogonality specified by $\mu$.
3. Residual: $F^{(0)} = \tilde{Y} - \tilde{G}(H^{(0)}) \hat{X}^{MNE}(\tilde{Y}, \tilde{G}(H^{(0)}), \tilde{R})$
   Iteration starting at l=1:
1. Support Expansion: $H^{(l)} = H^{(l-1)} \cup \{L$ rows in $\hat{X}^{MNE} (F^{(l-1)}, \tilde{G}, \tilde{R})$ with largest $l_{2-norms}$ satisfying the degree of orthogonality specified by $\mu\}$.
2. Estimation on Expanded Support: $Z^{(l)} = \hat{X}^{MNE}(\hat{Y}, \hat{G}(H^{l}), \tilde{R})$.
3. Support Trimming: Update $H^{(l)}$ to L rows in $Z^{(l)}$ with largest $l_{2-norms}$ satisfying the degree of orthogonality specified by $\mu$.
4. Residual Update: $F^{(l)} = \tilde{Y} - \tilde{G}(H^{(l)}) \hat{X}^{MNE}(\tilde{Y}, \tilde{G}(H^{(l)}), \tilde{R})$.
5. Stopping Criterion: If $H^{(l)} = H^{(l-1)}$, set outputs $H = H^{(l)}$ and $\hat{X}_H^{(end)} = \hat{X}^{MNE}(Y, \tilde{G}(H^{(l)}), \tilde{R})$ and end iterations.

The final H specifies the subset of regions in the source space that are most relevant to the measurement, while $\hat{X}_H^{(end)}$ specifies the currents in modes of the forward solutions of these regions. Note that the $\hat{X}_H^{(end)}$ is unit-less as the forward solutions are scaled by current strengths. To interpret the regional currents on the same units scale and in physical dipole coordinates, all $\hat{X}_H^{(end)}$ were scaled by the current strength c and projected back into dipole space to obtain $\hat{X}_H = cW'\hat{X}_H^{(end)}$. Overall, this subspace pursuit algorithm offers an efficient means to iteratively concentrate the MNE into the few regions most "relevant" (in the minimum $l_2$-norm sense) to the measurement.

Data Analysis Across Hierarchies

The above MNE+subspace pursuit algorithm is repeated across hierarchies to yield estimates $\hat{X}_{H_J}$ at the final hierarchy. In practice, forward solutions can be computed across the hierarchies of source spaces and grouped by region. Time windows of interest can be selected based on latencies of expected features. The number of relevant regions or the target sparsity level L can be specified to reflect the spatial extent/number of regions expected to be active during a given paradigm. The same L can be maintained across hierarchies. The number of relevant regions can be pre-specified for convenience, or the algorithm could be rewritten to iteratively add one projection at a time until all significant field patterns in the measurement are explained and the residual is white across sensors. The procedure is very similar to employing a formal model selection and goodness of fit procedure. Both MEG and EEG recordings can be used for localization if simultaneous recordings are available. The two sets of recordings can be processed separately (filtering, averaging and covariance estimation), their forward solutions can be computed separately, and the measurement vectors and forward solutions can be concatenated after accounting for respective noise covariances separately for consistency of units. The final source current estimates $\hat{X}_{H_J}$ specifies the currents in modes of the forward solutions, and can be projected back into dipole space for reporting. Then, the estimated source currents can be summarized as vector resultant currents by region. Spatial brain activity maps, regional source current time courses and summary root mean square values of dipole source current estimates can be computed and displayed for understanding the regional distribution of current estimates.

Experimental Results

To validate the algorithm, auditory responses evoked with a train of click stimuli were analyzed during resting eyes open condition. Auditory responses were chosen because these responses comprise distinct M/EEG peaks and established latencies corresponding to a stereotypical progression of activity from the cochlea, through inferior colliculus to medial geniculate thalamus and auditory cortex, and thus serve as a good testcase for validating a subcortical source localization algorithm. Simultaneous M/EEG auditory evoked recordings (AEPs) were obtained during binaural stimulation and corresponding anatomic MRI using the paradigm described below.

Simultaneous MEG and EEG AEP recordings, and structural MRIs were obtained on two healthy volunteers aged 25-45 years screened for standard MRI contraindications and normal audiometry (no evidence of hearing loss in 0-4 kHz range). A train of broadband clicks having 0.1 msec duration, intensity 65-80 dB/nHL and inter-stimulus interval 110 msec (click rate 9.09 Hz, corresponding to highest AEP SNR), generated within the Presentation™ software (Version 17.1, Neurobehavioral Systems, Inc., Albany, Calif., USA), was delivered binaurally during eyes open resting condition. Subjects were asked to sit still, not pay any attention to the sounds and imagine a dot at the center of the screen. M/EEG data were recorded at 5 kHz sampling with filter cutoffs set to 0.03-1660 Hz. After acquiring 2 min of pre-stimulus baseline eyes open data, AEPs were recorded in 5 runs of 5.5 min each, yielding 10000-16000 epochs for averaging. At the start of each run, standard checks were performed to ensure no stimulus artifacts, subjects were allowed a blink break if needed, and HPI recordings were obtained. Non-stimulus baseline recordings were repeated at the end of the study and MEG empty-room recordings were also obtained. The study was approved by the Partners Human Research Committee at Massachusetts General Hospital, and written informed consent was obtained from all subjects.

The raw data were preprocessed to remove power line noise using a comb notch filter (MATLAB™) with 30 notches at harmonics of 60 Hz, each having bandwidth 1 Hz. Artifactual channels (marked by inspection) and eye-blink epochs (peak to peak EOG<150 uV in 1-40 Hz band) were both excluded. The early auditory brainstem response (ABR) and later middle latency response (MLR) components of the auditory evoked potential were processed separately by band-pass filtering the preprocessed data to 500-1625 Hz, and 30-300 Hz respectively. In each case, the data were processed to (a) compensate for interference, (b) obtain stimulus locked average evoked responses, and (c) estimate noise covariances. First, standard signal space projections (SSP), computed using principal component analysis on the empty room MEG recordings, were used to compensate for environmental interference. Second, stimulus timings to denote epochs for averaging were compensated for a sound tube delay of 9.775 msec (as measured by recording sounds delivered at the ear piece with an optical microphone). Grand averages across runs were performed without HPI correction if HPI head coordinates across runs were within 2%. Overall, a total of 11200 epochs were used for the averages considered in our analysis. Third, observation noise covariances were estimated using the baseline eyes open recording. These data give a good measure of background "noise" arising from ongoing brain activity and systematic instrumental disturbances. As the MEG noise covariance is typically ill-conditioned, external disturbances to the covariance estimate were suppressed by applying the SSP operator, and then diagonal loading was applied. All SSP, averaging and covariance calculations were performed in bands relevant to components of interest.

Figures 7A, 7B:
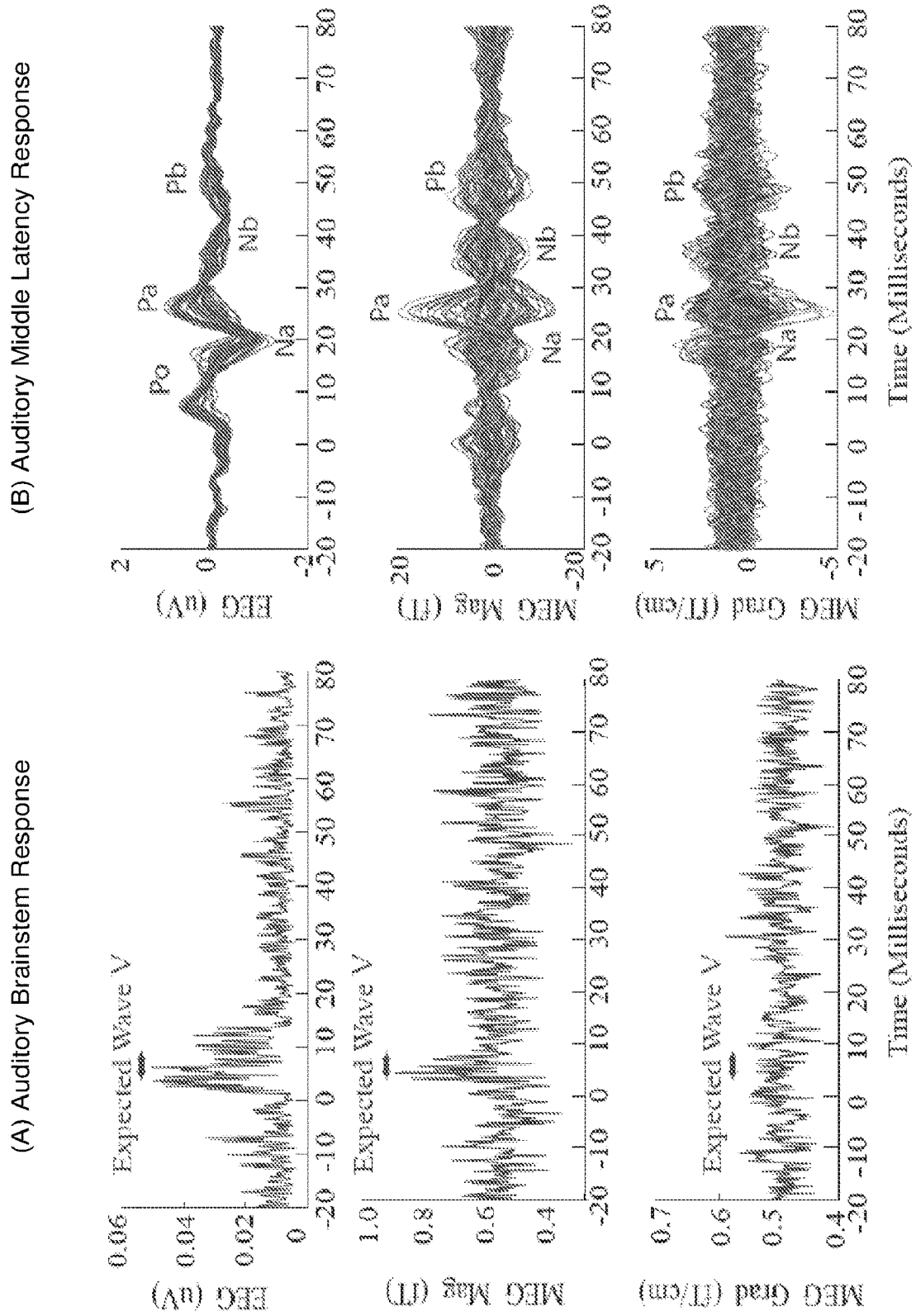
FIGS. 7A-B illustrate auditory evoked response recordings obtained to validate the efficacy of the deep brain imaging approach presented above. Each panel presents stimulus-locked average auditory evoked responses obtained on a healthy volunteer presented with a broadband click train stimulus. Data shown are averages across 11200 epochs. (A) Auditory brainstem responses—the red bar marks periods when early peaks are seen in the data, the timing of these peaks is consistent with expected location of wave V. Time courses are raw recordings filtered 500-1625 Hz, rectified and averaged across channels. (B) Middle latency responses. Common peaks are marked and latencies follow known trends. Time courses are raw recordings filtered 0-300 Hz, displayed across multiple channels.
Figure 8A:
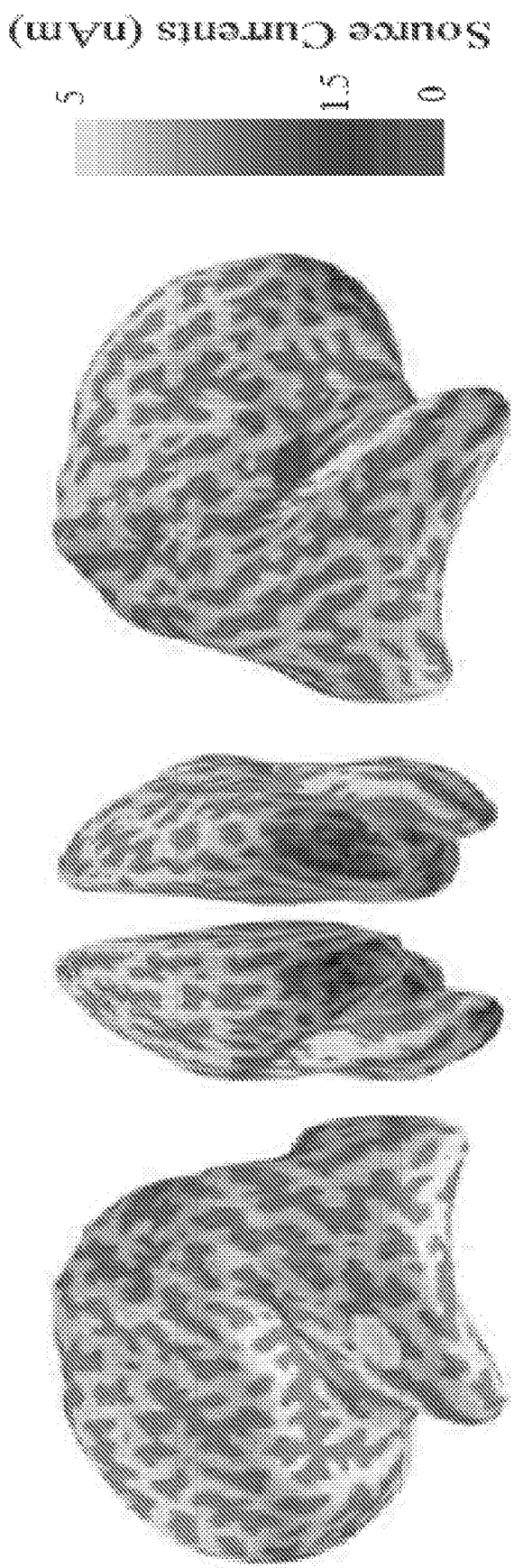
Figure 8D:
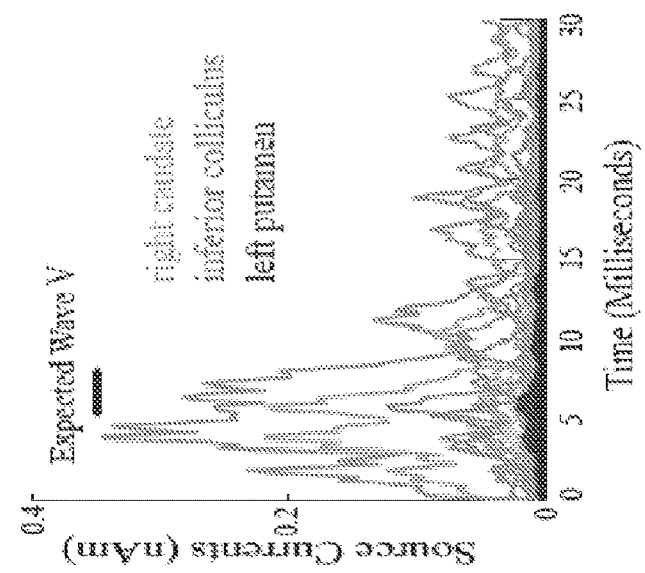
Figure 8E:
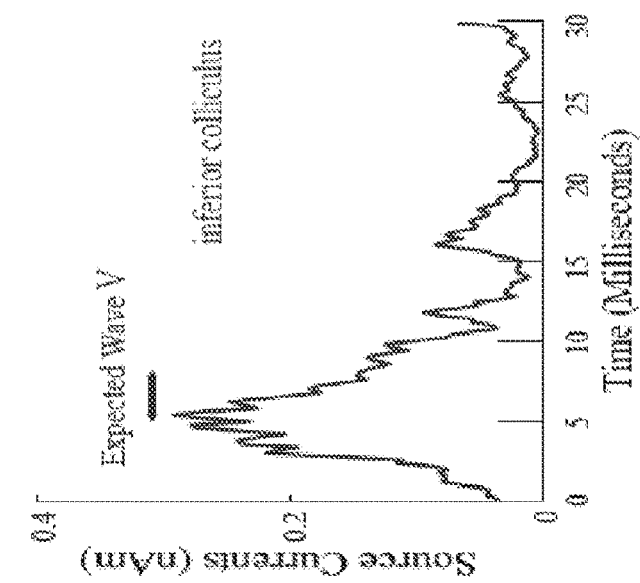
Figure 8F:
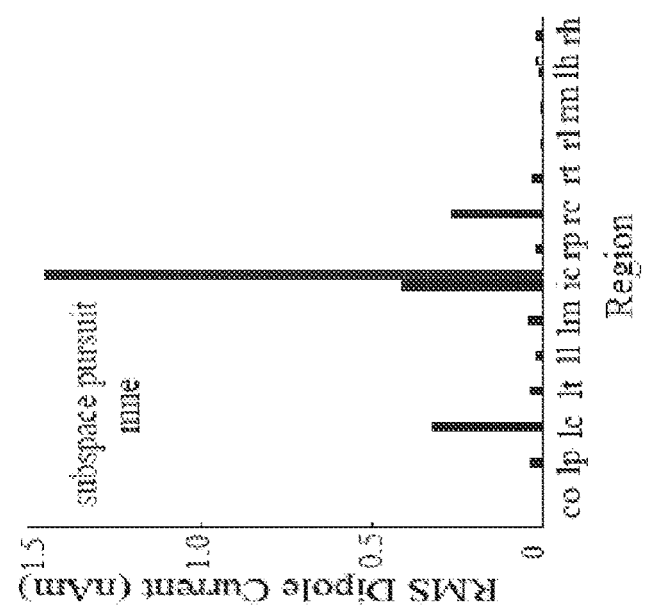

FIGS. 7A-B summarize the M/EEG evoked responses. The early auditory brainstem responses (ABR) are shown in FIG. 7A, while later middle latency responses (MLR) are in FIG. 7B.

Examining FIG. 7A, we note that the EEG ABRs have higher SNR than MEG ABRs. Thus marking the early peaks on EEG and looking for coincidental peaks in the MEG recordings, we see that the MEG magnetometers also show ABRs at the expected latencies while the gradiometers do not exhibit significant features at these latencies. While it is difficult to resolve individual early waves corresponding to cochlear nucleus and lower brainstem structures like the superior olivary complex, there is clear evidence of evoked peaks in the 5-7 msec time range, which is consistent with the expected timing (5.6-5.8 msec) of the brainstem wave V known to arise from inferior colliculus. Proceeding to the MLR in FIG. 3-8B, we see that the EEG has a low amplitude Po feature, which is thought to mark the end of brainstem components and potentially the start of thalamic components. However, Po is not seen clearly on the MEG and the thalamic involvement at these latencies is controversial and has not been resolved to date. Peaks Na-Pa reflect classic middle latency activity in the (supratemporal) primary auditory cortex (A1). Peaks beyond 40 msec reflect activity in secondary auditory cortices and higher association regions. Thus, as the most prominent peaks with well-known locations are the early brainstem wave V and the later Na-Pa peaks, we asked if source localization can reveal activity in (a) inferior colliculus during 5-7 msec, and (b) A1 during 20-30 msec.

FIG. 8 illustrates the spatial maps and time courses of source estimates obtained on the auditory evoked responses. FIG. 8A shows localization of MLR peaks (Na-Pa) to bilateral primary auditory cortices (A1). These areas comprise the reduced cortical source space Csp, which along with the subcortical volume sources S, form the combined source space J for final estimation. We focus on describing estimates for the early ABR components where subcortical structures are activated. FIG. 8B-D illustrates spatial maps and time courses of the estimates within source space J. Subspace pursuit estimates (FIG. 8B) localize specifically to inferior colliculus, while MNE estimates (FIG. 8C) localize both to inferior colliculus and sources in caudate and thalamus (with the latter estimates having higher amplitude than the former). FIG. 8D quantitatively summarizes the regional distributions of dipole current amplitudes by region—showing that SP refines the non-specific MNE estimate to concentrate activity into the most relevant regions. Time courses of the SP and MNE estimates are in FIG. 8E-F. SP estimates of activity in inferior colliculus peak at the time interval where wave 5 is expected. As the number of relevant regions L was set to 1 (only 1 key region is expected to be active during 0-10 msec), the sparse estimate shows only one time course. The MNE estimates show activity in multiple regions peaking at the time intervals of interest, making it hard to discern specific activity expected in inferior colliculus.

Finally, all the above estimates were obtained using both MEG and EEG data (where EEG has higher SNR wave 5 peaks). Accuracy was also effectively validated on unimodal MEG data, which has lower SNR, showing that the algorithm does not rely on having high amplitude peaks or high SNR in the data.

Although specific embodiments are described above, it will be apparent to those of ordinary skill that a number of variations can be made within the scope of the disclosure. For example, it will be apparent that processing equipment and hardware can be used to perform the data acquisitions, and data analysis methods, processes, and algorithms described above. Computing equipment for performing these tasks can include a processor; various types of memory components; user input devices, such as keyboards, mice, and data input drives; and output devices such as displays, printers, and data transmission devices. These components can be provided as part of a medical imaging system, in a network connected to a medical imaging system, as a stand-alone system, or as part of a network. Although flow charts illustrating steps are provided and described above, these charts are by way of illustration. The steps shown in any given flow chart are not required in all cases, and the order of the steps can, in some cases, be varied. It should be understood, therefore, that the methods and apparatuses described above are only exemplary and do not limit the scope of the invention, and that various modifications could be made by those skilled in the art that would fall within the scope of the invention. To apprise the public of the scope of this invention, the following claims are made:

We claim:

1. A method for non-invasively characterizing electrophysiological activity within deep brain regions based on data measurements acquired during a functional task of interest, the method comprising:
  acquiring measured data representative of brain activity of a subject during a functional task of interest,
  acquiring magnetic resonance images of brain anatomy of the subject,
  constructing superficial (cortical) source spaces and deep (subcortical) source spaces for regions of the brain from the magnetic resonance images, the cortical source spaces including a first set of cortical source spaces having patches with a first size, a second set of cortical source spaces having patches with a second size, the second size being smaller than the first size;
  determining a first relationship between the source spaces and the measured data;
  determining a minimum norm source current estimate (MNE) based on the source spaces, the first relationship, and the measured data, the MNE including a first subset of source spaces;
  refining the MNE a first time by using and determining a second relationship between the measured data, and cortical source spaces from the second set of cortical source spaces that at least partially overlap with the first subset of source spaces, the refined MNE including a second subset of source spaces, the second subset of source spaces including a cortical source space;

further refining the MNE by using and determining a third relationship between the second subset of source spaces, the subcortical source spaces, and the measured data, the further refined MNE including a superficial source space and a deep source space that underlies the measured data.

2. The method of claim 1, wherein the measured data is obtained by at least one of an electroencephalography (EEG) and an magnetoencephalography (MEG).

3. The method of claim 1, wherein constructing source spaces from the magnetic resonance images of brain anatomy of the subject includes positioning dipoles within a given source space, and wherein at least one source space corresponds to at least one of: a neocortex, a hippocampus, a gray-white matter interface, and a subcortical volume.

4. The method of claim 1, wherein each cortical source space is a surface patch having dipoles, and wherein the subcortical source spaces include volume subdivisions and surface patches having dipoles.

5. The method of claim 4, wherein the surface patches and volume subdivisions are sized to homogenize current strengths.

6. The method of claim 4, wherein the surface patches and the volume subdivisions having high current densities are assigned finer subdivisions, and wherein the surface patches and the volume subdivisions having low current densities are assigned larger subdivisions to homogenize current strengths thereby enabling comparable consideration of the surface patches and volume subdivisions in an inverse solution.

7. The method of claim 1, wherein determining the second relationship includes searching for cortical source spaces within the second set of cortical source spaces that at least partially overlap with the first subset of source spaces that correlate to the measured data with least residual error to determine the second subset of source spaces.

8. The method of claim 1, wherein constructing cortical source spaces includes constructing a third set of cortical source spaces having patches with a third size, the third size being smaller than the first size and the second size, and further comprising refining the MNE a second time by using and determining a relationship between the measured data, and cortical source spaces from the third set of cortical source spaces that at least partially overlap with the second subset of source spaces, the refined MNE from the second time including a third subset of source spaces, the third subset of source spaces including a cortical source space, and wherein further refining the MNE includes using and determining a fourth relationship between the third subset of source spaces, the subcortical source spaces, and the measured data, to identify the superficial source space and the deep source space that underlies the measured data.

9. The method of claim 8, wherein the cortical source spaces from the second set of cortical source spaces that at least partially overlap with the first subset of source spaces include cortical source spaces from the second set of cortical source spaces that are closely located to the first subset of source spaces.

10. A method for imaging electromagnetic sources within deep brain structures based on M/EEG data identified while a subject is performing a functional task of interest, the method comprising:

constructing source spaces in superficial (cortical) and deep (subcortical) regions of the brain from images of the brain, the source spaces including a first set of patches of the superficial and deep regions of a first preselected level of coarseness, and a second set of patches at a second preselected level of coarseness, each of the patches in each set being sized to homogenize current strengths, and wherein the first set of patches and the second set of patches span across the same surface;

relating the source spaces with the M/EEG data;

computing a minimum norm source current estimate (MNE) based on the relationship between the source spaces and the M/EEG data, the source spaces, and the M/EEG data, refining the MNE by iteratively reducing and expanding a subset of source spaces that are defined within the MNE to identify at least one superficial and at least one deep source whose activity underlies the M/EEG data.

11. The method of claim 10, wherein the homogenization of the patches enables weaker and stronger gain regions to have comparable consideration in an inverse solution.

12. The method of claim 10, wherein refining the MNE includes determining a correlation between a neighboring source space and a given source space within the subset of source spaces.

13. The method of claim 12, further comprising comparing the correlation to a mutual coherence threshold, wherein the neighboring source space is included in the MNE, based on the correlation being less than the mutual coherence threshold, and wherein the neighboring source space is excluded from the MNE, based on the correlation being greater than the mutual coherence threshold.

14. A method for electromagnetic source imaging based on non-invasive M/EEG recordings and MM-based anatomic measures to employ information within M/EEG field patterns for estimating source currents across superficial and deep brain regions, the method comprising:

constructing source spaces, the source spaces including a first set of cortical source spaces having patches with a first size, a second set of cortical source spaces having patches with a second size, and a third set of subcortical source spaces having a third size, wherein the second size being smaller than the first size, and wherein the first set of source spaces and the second set of source spaces span across the same surface;

computing a minimum norm source current estimate (MNE) using the source spaces and the non-invasive M/EEG recordings;

iteratively refining the MNE until the MNE includes a subset of source spaces having at least one superficial and at least one deep source whose activity underlies the non-invasive M/EEG recordings.

15. The method of claim 14, wherein the iterative refinement of the MNE includes:

comparing the first set of cortical source spaces and the M/EEG recordings to determine a first subset of cortical source spaces;

determining a second set of cortical source spaces, the second set of cortical source spaces being from the second set of cortical source spaces, the second set of cortical source spaces at least partially overlapping with the first subset of cortical source spaces; and determining a second subset of cortical sources spaces within the second set of cortical source spaces using the M/EEG recordings, the second subset of cortical sources determining the subset of source spaces.

16. The method of claim 14, further comprising acquiring magnetic resonance images of the brain and using the images to construct the source spaces in for the cortical and subcortical regions of the brain.

17. The method of claim 14, wherein the third set of subcortical source spaces include a plurality of subcortical volume subdivisions.

18. The method of claim 17, wherein the patches of the first set of cortical source spaces and the plurality of subcortical volume subdivisions of the third set of subcortical source spaces are sized to have homogenous current strength.

19. A subspace pursuit process for characterizing electrophysiological activity within deep brain regions based on non-invasive M/EEG measurements, the pursuit process being performed on a plurality of source spaces, the source spaces including a plurality of cortical surface patches and subcortical volume subdivisions for regions of the brain, the process comprising:

acquiring measured data representative of brain activity of a subject, the measured data being indicative of electrophysiology activity within deep brain regions of the subject;

computing a minimum norm source current estimate (MNE) using the cortical surface patches and the measured data;

refining the MNE by performing a subspace pursuit to identify a first cortical surface patch that correlates to the measured data, the first cortical surface patch having a first size;

further refining the MNE by performing a second subspace pursuit on a subset of cortical surface patches each having second size to determine a second cortical surface patch that correlates to the measured data, the second cortical surface patch being smaller than the first cortical surface patch and the subset of cortical surface patches, the second size being smaller than the first size, the subset of cortical surface patches at least partially overlapping with the first cortical surface patch; and performing a third subspace pursuit between the second cortical surface patch and the subcortical volume subdivisions to determine cortical and subcortical brain regions whose activity correlate best to the measured data.

20. The process of claim 19, wherein the patches are sized, such that a given patch has a first current strength and a second patch has a second current strength, and wherein the first current strength and the second current strength are homogenous.

* * * * *

UNITED STATES PATENT AND TRADEMARK OFFICE
CERTIFICATE OF CORRECTION

PATENT NO. : 10,716,485 B2
APPLICATION NO. : 15/521987
DATED : July 21, 2020
INVENTOR(S) : Pavitra Krishnaswamy et al.

It is certified that error appears in the above-identified patent and that said Letters Patent is hereby corrected as shown below:

In the Specification

Column 9, Line 64, "c=ρA" should be --c = σA--.

Column 10, Line 17, " $\frac{\sum_{b=1}^{P} S_{bb}}{\sum_{b=1}^{B} S_{bb}} \geq 0.95$ " should be -- $\frac{\sum_{b=1}^{P} S_{bb}}{\sum_{b=1}^{B} S_{bb}} \geq 0.95$ --.

Column 10, Line 45, " $\hat{G}'_i \hat{G}_j = Up_{i,j} \sum_{i,j} Wp_{i,j}$ " should be -- $\hat{G}'_i \hat{G}_j = Up_{i,j} \sum_{i,j} Wp_{i,j}$ --.

Column 10, Line 47, " $\sum_{i,j} = diag(s_1, s_2, \ldots s_n)$ " should be -- $\sum_{i,j} = diag(s_1, s_2, \ldots s_n)$ --.

Column 13, Lines 37-38, "$G_J = [\mathbb{C}_{sp}, G_S]$" should be --$G_J = [G\mathbb{C}_{sp}, G_S]$--.

In the Claims

Column 20, Claim 14, Line 41, "MM-based" should be --MRI-based--.

Signed and Sealed this
Eighth Day of September, 2020

Andrei Iancu
*Director of the United States Patent and Trademark Office*